United States Patent
Renn et al.

(10) Patent No.: US 10,272,017 B2
(45) Date of Patent: Apr. 30, 2019

(54) AQUEOUS DENTAL GLASS IONOMER COMPOSITION

(71) Applicant: DENTSPLY SIRONA Inc., York, PA (US)

(72) Inventors: Caroline Renn, Singen (DE); Oliver Elsner, Radolfzell (DE); Florian Szillat, Constance (DE); Joachim Klee, Radolfzell (DE); Christoph Weber, Constance (DE); Uwe Walz, Constance (DE); Christian Scheufler, Engen (DE); Andrew Lichkus, York, PA (US); Xiaoming Jin, Middletown, DE (US)

(73) Assignee: DENTSPLY SIRONA Inc., York, PA (US)

( * ) Notice: Subject to any disclaimer, the term of this patent is extended or adjusted under 35 U.S.C. 154(b) by 0 days.

(21) Appl. No.: 15/486,342

(22) Filed: Apr. 13, 2017

(65) Prior Publication Data

US 2017/0296442 A1   Oct. 19, 2017

Related U.S. Application Data

(60) Provisional application No. 62/323,063, filed on Apr. 15, 2016.

(51) Int. Cl.
| | | |
|---|---|---|
| *C08F 2/46* | (2006.01) | |
| *C08F 2/50* | (2006.01) | |
| *C08G 61/04* | (2006.01) | |
| *A61K 6/083* | (2006.01) | |
| *A61K 6/00* | (2006.01) | |

(52) U.S. Cl.
CPC .......... *A61K 6/0835* (2013.01); *A61K 6/0052* (2013.01); *A61K 6/0091* (2013.01); *A61K 6/083* (2013.01)

(58) Field of Classification Search
CPC .... A61K 6/0052; A61K 6/083; A61K 6/0835; A61K 6/0091; C08L 33/00; C08L 33/08; C08L 33/10
USPC .......... 522/39, 33, 6, 71, 189, 184, 1; 520/1
See application file for complete search history.

(56) References Cited

U.S. PATENT DOCUMENTS

| | | | | |
|---|---|---|---|---|
| 2012/0077901 A1* | 3/2012 | Tanaka | .............. | A61K 6/0835 523/116 |
| 2013/0289216 A1* | 10/2013 | Klee | .............. | A61K 6/0835 525/285 |
| 2014/0039088 A1* | 2/2014 | Stelzig | .............. | A61K 6/0023 523/116 |

FOREIGN PATENT DOCUMENTS

JP   2014-181190   * 9/2014

OTHER PUBLICATIONS

Takei et al, JP 2014-181190 Machine Translation, Sep. 24, 2014 (Year: 2014).*

* cited by examiner

*Primary Examiner* — Jessica Whiteley
(74) *Attorney, Agent, or Firm* — Dentsply Sirona Inc.

(57) ABSTRACT

An aqueous dental glass ionomer composition comprising (A) a reactive particulate glass, (B) a water-soluble polymer comprising acidic groups, which is reactive with the particulate glass in a cement reaction, (C) a water-soluble, hydrolysis-stable monomer having a single polymerizable double bond and optionally a carboxylic acid group or hydroxyl group; (D) a water-soluble, hydrolysis-stable polymerizable crosslinker having at least two polymerizable carbon-carbon double bonds; and (E) a polymerization initiator system.

20 Claims, No Drawings

AQUEOUS DENTAL GLASS IONOMER COMPOSITION

FIELD OF THE INVENTION

The present disclosure relates to an aqueous dental glass ionomer composition.

The aqueous dental glass ionomer composition according to the present disclosure provides a cured glass ionomer composition having excellent mechanical properties and long-term mechanical and chemical resistance.

BACKGROUND

Dental restorative materials are known for restoring the function, morphology and integrity of dental structures damaged by physical damage or caries-related decay of enamel and/or dentin. Dental restorative materials are required to have high biocompatibility, good mechanical properties and mechanical and chemical resistance over a long period of time.

Dental restorative materials include glass ionomer cements having good biocompatibility and good adhesion to the dental hard tissues. Moreover, glass ionomer cements may provide cariostatic properties through the release of fluoride ions. Glass ionomer cements are cured by an acid-base reaction between a reactive glass powder and a polyalkenoic acid. However, conventional glass ionomer cements have a relatively low flexural strength and are brittle due to salt-like structures between the polyacid and the basic glass.

The mechanical properties of glass ionomer cements may be improved by the selection of the combination of the polyacidic polymer and polymerizable compounds in the aqueous dental glass ionomer composition.

WO 03/011232 A1 discloses water-based dental glass ionomer cements mandatory containing two types of polymers, namely a first polymer having a plurality of acidic repeating units but being substantially free of polymerizable vinyl groups, and a second polymer having a plurality of acidic repeating units and a plurality of polymerizable vinyl groups. The dental glass ionomer cement may contain α,β-unsaturated monomers selected from the group consisting of water-soluble, water-miscible or water-dispersible acrylates and methacrylates such as 2-hydroxyethyl methacrylate, 2-hydroxypropyl methacrylate, tetrahydrofurfuryl methacrylate, glycerol mono- or di-methacrylate, trimethylol propane trimethacrylate, ethylene glycol dimethacrylate, polyethylene glycol dimethacrylate, urethane methacrylates, acrylamide, methacrylamide, methylene bis-acrylamide or methacrylamide, diacetone acrylamide, methacrylamide, glycerol phosphate monomethacrylates, glycerol phosphate dimethacrylates, hydroxyethyl methacrylate phosphates and citric acid di- or tri-methacrylates.

WO 93/016676 A1 discloses water-based dental glass ionomer cements from β-dicarbonyl polymers. The dental glass ionomer cements contain a polymer comprising i) pendant β-dicarbonyl groups, such as β-diesters, β-diketones or β-ketoesters, capable of undergoing a setting reaction in the presence of water, and a reactive powder, and ii) optionally an ionic group, such as a carboxyl group, capable of undergoing a setting reaction in the presence of water and a reactive powder. Additionally, the dental glass ionomer cements may optionally contain copolymerizable cosolvents such as 2-hydroxylethylmethacrylate or 2-hydroxypropylmethacrylate. In an experimental example, alternatively to these copolymerizable cosolvents, tetraacrylamidomethyl glycouril is contained in the dental glass ionomer cement.

SUMMARY

It is an object of the present disclosure to provide an aqueous dental glass ionomer composition providing improved mechanical properties including high flexural strength and providing a clinically relevant adhesion to tooth structure after curing, as well as hydrolysis-stability in an aqueous medium before and after curing, in particular in an acidic medium.

The present disclosure provides an aqueous dental glass ionomer composition comprising
  (A) a reactive particulate glass,
  (B) a water-soluble polymer comprising acidic groups, which is reactive with the particulate glass in a cement reaction,
  (C) a water-soluble, hydrolysis-stable monomer having a single polymerizable double bond and optionally a carboxylic acid group or hydroxyl group;
  (D) a water-soluble, hydrolysis-stable polymerizable crosslinker having at least two polymerizable carbon-carbon double bonds; and
  (E) a polymerization initiator system.

A cured aqueous dental glass ionomer composition according to the present disclosure has hydrolysis-stability and excellent mechanical properties based on the specific combination of the polymer according to (B), the water-soluble, hydrolysis-stable monomer having a single polymerizable double bond according to (C) and the water-soluble, hydrolysis-stable polymerizable crosslinker having at least two polymerizable carbon-carbon double bonds according to (D). Upon polymerization of the monomer according to (C) and the crosslinker according to (D), a crosslinked copolymer is obtained into which the polymer according to (B) is incorporated.

The inventors have recognized that resin reinforced dental glass ionomer cements are subject to deterioration during storage or after curing in the mouth of the patient. The inventors have further recognized that the deterioration includes hydrolytic degradation of the resin component conventionally containing hydrolyzable moieties. The inventors have then recognized that by using a specific aqueous dental glass ionomer composition comprising a polymer according to (B), a monomer according to (C) and a crosslinker according to (D), an improved aqueous dental glass ionomer composition may be obtained which upon curing provides at a mechanically and chemically stable dental cement which overcomes the drawbacks of conventional resin reinforced glass ionomer cements known from the prior art.

DETAILED DESCRIPTION OF EMBODIMENTS

In the following, sometimes components (A), (B), (C), (D) and (E) of the present aqueous dental glass ionomer composition are referred to by the terms "(reactive particulate) glass according to (A)", "(water-soluble,) polymer (comprising acid groups) according to (B)", "(water-soluble, hydrolysis-stable) monomer (having a single polymerizable double bond) according to (C)", (water-soluble, hydrolysis-stable) crosslinker (having at least tow polymerizable carbon-carbon double bonds) according to (D) and ("polymerization initiator system according to (E)" respectively.

The terms water-soluble, hydrolysis-stable monomer having "a single polymerizable double bond", the water-soluble, hydrolysis-stable crosslinker having "at least two polymerizable carbon-carbon bonds" and "compound having a polymerizable moiety" having "polymerizable pendant groups" respectively mean compounds capable of combining by covalent bonding in an addition polymerization to form a polymer.

The terms "a single polymerizable double bond" as used herein in connection with the monomer according to (C) and "at least two polymerizable carbon-carbon double bonds" as used herein in connection with crosslinker (D) of the present aqueous dental glass ionomer composition mean any double/carbon-carbon bond capable of addition polymerization, in particular free radical polymerization.

The term "curing" means the polymerization of functional monomers, oligomers or even polymers, into a polymer network.

The term "curable" refers to a aqueous dental glass ionomer composition that will polymerize into a crosslinked polymer network when irradiated for example with actinic radiation such as ultraviolet (UV), visible, or infrared radiation, or when reacted with polymerisation initiators.

The present aqueous dental glass ionomer composition provides a cured dental glass-ionomer composition/cement. Said cured dental glass ionomer composition/cement is formed based on a reaction between (A) the reactive particulate glass, the above described polymer components according to (B), monomer according to (C), crosslinker according to (D) and polymerization initiator system according to (E) in a cement reaction and a polyaddition reaction.

(A) The Reactive Particulate Glass

An aqueous dental glass ionomer composition according to the present disclosure comprises a reactive particulate glass. A reactive particulate glass is obtainable by transforming a mixture of metal oxides by a thermal melt process into a glass followed by milling, which glass is capable of reacting with a polymer containing acidic groups in a cement reaction. The glass is in particulate form. Moreover, the reactive particulate glass may be surface modified, e.g. by silanation or acid treatment. Any conventional reactive dental glass may be used for the purpose of the present disclosure. Specific examples of particulate reactive glasses are selected from calcium alumino silicate glass, calcium alumino fluorosilicate glass, calcium aluminumfluoroborosilicate glass, strontium aluminosilicate glass, strontium aluminofluorosilicate glass, strontium aluminofluoroborosilicate glass. Suitable particulate reactive glasses may be in the form of metal oxides such as zinc oxide and/or magnesium oxide, and/or in the form of ion-leachable glasses, e.g., as described in U.S. Pat. No. 3,655,605, 3,814,717, 4,143,018, 4,209,434, 4,360,605 and 4,376,835.

Preferably, the reactive particulate glass according to (A) is a reactive particulate glass comprising:
1) 20 to 45% by weight of silica,
2) 20 to 40% by weight of alumina,
3) 20 to 40% by weight of strontium oxide,
4) 1 to 10% by weight of $P_2O_5$, and
5) 3 to 25% by weight of fluoride.

The present aqueous dental glass ionomer composition preferably comprises 20 to 90 percent by weight of the reactive particulate glass, more preferably 30 to 85 percent by weight, most preferably 20 to 80 percent by weight based on the total weight of the composition.

The reactive particulate glass usually has an average particle size of from 0.1 to 100 μm, preferably of from 1 to 40 μm as measured, for example, by electron microscopy or by using a conventional laser diffraction particle sizing method as embodied by a MALVERN Mastersizer S or MALVERN Mastersizer 2000 apparatus.

The reactive particulate glass may have a unimodal or multimodal (e.g., bimodal) particle size distribution, wherein a multimodal reactive particulate glass represents a mixture of two or more particulate fractions having different average particle sizes.

The reactive particulate glass may be a an agglomerated reactive particulate glass which is obtainable by agglomerating a reactive particulate glass in the presence of a modified polyacid and/or polymerizable (meth)acrylate resins. The particle size of the agglomerated reactive particulate glass may be adjusted by suitable size-reduction processes such as milling.

The reactive particulate glass may be surface modified by a component according to (B), (C), (D) and/or (E). In particular, the reactive particulate glass may be surface modified by one or more components of the polymerization initiator system (E) in order to avoid contact of the one or more components of the polymerization initiator system (E) with an acid under aqueous conditions.

The reactive particulate glass may alternatively or additionally be surface modified by a surface modifying agent. Preferably, the surface modifying agent is a silane. A silane provides a suitable hydrophobicity to the reactive particulate glass, which allows for an advantageous, homogeneous admixture with the organic components according to (B), (C), (D) and (E) of the aqueous dental glass ionomer composition.

(B) The Water-Soluble Polymer Comprising Acidic Groups

The aqueous dental glass ionomer composition according to the present disclosure comprises a water-soluble polymer comprising acidic groups, which is reactive with the particulate glass in a cement reaction. The water-soluble polymer comprising acidic groups is an organic polymeric compound comprising ionizable pendant groups, such as carboxylic acid groups. The carboxylic acid groups of the polymer are capable of reacting with a reactive particulate glass in a cement reaction to form a glass ionomer cement.

The water-soluble polymer comprising acidic groups according to (B) is obtainable by a process comprising:
a) a step of (co)polymerizing a mixture comprising
    (i) a first polymerizable monomer comprising at least one optionally protected acidic group and a first polymerizable organic moiety and optionally
    (ii) a second copolymerizable monomer comprising one or more optionally protected primary and/or secondary hydroxyl and/or amino group(s) and a second polymerizable organic moiety,
    for obtaining a water-soluble polymer comprising acidic groups, and optionally
b) a step of coupling a compound having a functional group reactive with an acidic group of repeating units derived from the first polymerizable monomer and/or a functional group reactive with hydroxyl group of repeating units derived from the second copolymerizable monomer to the water-soluble polymer obtained in step a), wherein the optionally protected acidic group or hydroxyl and/or amino group(s) is/are deprotected.

Preferably, the "water-soluble polymer comprising acidic groups" according to (B) does not contain polymerizable groups such as polymerizable double bonds whereby such a polymer comprising acidic groups does not react with the water-soluble monomer according to (C) or the water-soluble, hydrolysis-stable polymerizable crosslinker according to (D). Rather, it is preferred that the water-soluble polymer comprising acidic groups is incorporated into a matrix of a polymer formed upon polymerization of the water-soluble monomer according to (C) and the water-soluble, hydrolysis-stable polymerizable crosslinker according to (D).

Further, the monomer according to (C) and the crosslinker according to (D) are hydrolysis-stable in order to obtain a polymer formed upon polymerisation of components (C) and (D) which polymer has chemical resistance to the conditions in the buccual cavity.

Accordingly, the mechanical properties and the long-term mechanical and chemical resistance of the cured aqueous dental glass ionomer composition is improved. Further, the water-soluble polymer comprising acidic groups according to (B) may be used for adjusting the viscosity of the uncured aqueous dental glass ionomer composition.

The term "water-soluble" used in connection with the polymer according to (B) and monomer according to (C) means that at least 0.1 g, preferably 0.5 g of the polymer or monomer dissolves in 100 g of water at 20° C.

According to the present disclosure, one or a mixture of two or more monomers according to (i) and/or (ii) may be used for preparing the water-soluble polymer comprising acidic groups by means of (co)polymerization.

After (co)polymerizing a mixture according to (i) and optionally (ii), to the thus obtained water-soluble polymer comprising acidic groups a compound may optionally be coupled which has a functional group reactive with an optionally protected acidic group of repeating units derived from the first polymerizable monomer or an optionally protected hydroxyl and/or amino group of repeating units derived from the second copolymerizable monomer in the water-soluble polymer comprising acidic groups. Preferably, said compound does not comprise polymerizable groups such as polymerizable carbon-carbon double bonds. The optionally protected acidic group and the optionally protected hydroxyl and/or amino group are at least partially deprotected, so that the pendant groups are linked to the backbone by ester groups, urethane groups and/or amide groups. Preferably, the pendant groups are non-polymerizable, that is they have no polymerizable group such as a polymerizable carbon-carbon double bond. The deprotection of the protected acidic group, the protected hydroxyl and/or amino group may be carried out after step a) and/or after step b).

According to the present disclosure, one or a mixture of two or more compound(s) having a functional group reactive with an optionally protected acidic group of repeating units derived from the first polymerizable monomer or an optionally protected hydroxyl and/or amino group of repeating units derived from the second copolymerizable monomer may be used for coupling these compounds to the water-soluble polymer comprising acidic groups.

The first polymerizable monomer to be used according to (i) comprises at least one, preferably one to three, more preferably one or two, most preferably one optionally protected acidic group(s).

Preferably, the acidic groups of the water-soluble polymer according to (B) are selected from carboxylic acid groups, phosphoric acid ester groups, phosphonic acid groups and sulfonic acid groups.

The protecting group of an optionally protected acidic group of the water-soluble polymer according to (B) is not particularly limited as long as it is a protecting group known to those of ordinary skill in the art of organic chemistry (cf. e.g. P. G. M. Wuts and T. W. Greene, Greene's Protective Groups in Organic Synthesis, 4th Edition, John Wiley and Sons Inc., 2007). For example, for acidic groups in the form of carboxylic acid groups, the protecting group is preferably selected from a trialkylsilyl group, an alkyl group and an arylalkyl group. More preferably, the protecting group for the carboxylic acid group is selected from an alkyl group or an arylalkyl group. Most preferably, the protecting group for the carboxylic acid group is selected from a tert-butyl group and a benzyl group. In one embodiment, the carboxyl-protecting group is a tert-butyl group.

In an embodiment of the aqueous dental glass ionomer composition of the present disclosure, the first polymerizable monomer according to (i) of step a) comprises at least one optionally protected acidic group in the form of a carboxylic acid group. It is preferred that this first polymerizable monomer is represented by the general formula (1a):

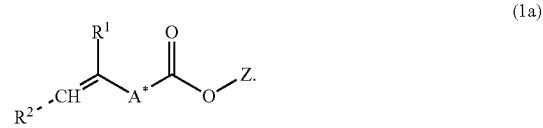

In formula (1a), $R^1$ is a hydrogen atom, a —COOZ group, a linear $C_{1-6}$ or branched or cyclic $C_{3-8}$ alkyl group which may be substituted with a —COOZ group, or a $C_{6-10}$ aryl group which may be substituted with a —COOZ group. Preferably, $R^1$ is a hydrogen atom, a —COOZ group or a methyl group. More preferably, $R^1$ is a hydrogen atom or a methyl group.

For $R^1$, a $C_{6-10}$ aryl group may, for example, be a phenyl group or a naphtyl group.

In formula (1a), $R^2$ is a hydrogen atom, a —COOZ group, or a linear $C_{1-6}$ or branched or cyclic $C_{3-8}$ alkyl group which may be substituted with a —COOZ group. Preferably, $R^2$ is a hydrogen atom or a —COOZ group. More preferably, $R^2$ is a hydrogen atom.

In formula (1a), the dotted line indicates that $R^2$ may be in either the cis or trans orientation relative to the moiety -A*-COOZ.

In formula (1a), A* is a single bond or a linear $C_{1-6}$ or branched or cyclic $C_{3-8}$ alkylene group, wherein if the carbon number of the alkylene group is two or more, then the alkylene group may contain 1 to 3 heteroatoms, wherein each heteroatom is located in between two carbon atoms of the alkylene carbon chain, which heteroatoms are selected from an oxygen atom, nitrogen atom, and sulfur atom, and/or which alkylene group may contain, if its carbon number is two or more, in between two carbon atoms of the alkylene carbon chain 1 to 3 groups selected from an amide bond or a urethane bond. Preferably, A* is a single bond or a linear $C_{1-6}$ or branched or cyclic $C_{3-8}$ alkylene group wherein if the carbon number of the alkylene group is two or more, then the alkylene group may contain a heteroatom in between two carbon atoms of the alkylene carbon chain, which heteroatom is selected from an oxygen atom or a nitrogen atom, and/or which alkylene group may contain, if its carbon number is two or more, in between two carbon atoms of the alkylene carbon chain a group selected from an amide bond or a urethane bond. More preferably, A* is a single bond or a straight-chain $C_{1-6}$ alkylene group. Most preferably, A* is a single bond.

In formula (1a), Z which may be the same or different, independently represents a hydrogen atom, a metal ion, a protecting group for a carboxylic acid group, or the Z forms with a further —COOZ group present in the molecule an intramolecular anhydride group. The metal ion may be a monovalent metal ion such as an alkali metal ion. In one embodiment, Z is a protecting group for a carboxylic acid group. In another embodiment, Z is a hydrogen atom. When Z forms with a further —COOZ group present in the molecule an intramolecular anhydride group (—C(O)OC(O)—), the further —COOZ group may be preferably present on $R^1$ such as in case of itaconic acid anhydride.

In an embodiment, Z is a hydrogen atom and the polymerization reaction is conducted in an alkaline environment. In an alternative embodiment, Z is a hydrogen atom and the carboxylic acid groups of the first polymerizable monomer and/or the hydroxyl groups of the second copolymerizable monomer carry a protecting group.

According to one embodiment of the present disclosure, the first polymerizable monomer is a compound represented by the general formula (1a'):

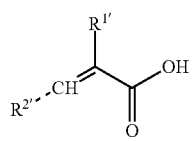

wherein $R^{1'}$ is a hydrogen atom or a linear $C_{1-4}$ or branched or cyclic $C_{3-6}$ alkyl group which may be substituted with a —COOH group, $R^{2'}$ is a hydrogen atom or a linear $C_{1-4}$ or branched or cyclic $C_{3-6}$ alkyl group which may be substituted with a —COOH group, preferably $R^{1'}$ and $R^{2'}$ are selected with the proviso that the molecular weight of the first polymerizable monomer is at most 200 Da, preferably at most 150 Da.

It is preferred that compound of formula (1a') is selected from the group consisting of itaconic acid, (meth)acrylic acid, maleic acid or an anhydride thereof. More preferably, compound of formula (1a') is (meth)acrylic acid or the intramolecular anhydride of itaconic acid or maleic acid. Most preferably, the compound of formula (1a') is acrylic acid or the intramolecular anhydride of itaconic acid.

According to another embodiment of the present disclosure, the first polymerizable monomer is a compound represented by the general formula (1a"):

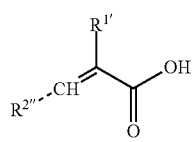

wherein $R^{1'''}$ is a hydrogen atom or a linear $C_{1-3}$ or branched $C_{3-5}$ alkyl group, and $R^{2'''}$ is a hydrogen atom or a linear $C_{1-3}$ or branched $C_{3-5}$ alkyl group which may be substituted with a —COOH group, wherein $R^{1'''}$ and $R^{2'''}$ are selected with the proviso that the molecular weight of the compound of formula (1") is at most 200 Da;

preferably, $R^{1'''}$ is a hydrogen atom, and $R^{2'''}$ is a hydrogen atom or a linear $C_{1-3}$ or branched $C_{3-5}$ alkyl group optionally substituted with a —COOH group, wherein $R^{1'''}$ and $R^{2'''}$ are selected with the proviso that the molecular weight of the compound of formula (1") is at most 150 Da;

more preferably, $R^{1'''}$ is a hydrogen atom, and $R^{2'''}$ is a hydrogen atom or a methyl group substituted with a —COOH group, wherein $R^{1'''}$ and $R^{2'''}$ are selected with the proviso that the molecular weight of the compound of formula (1a") is at most 150 Da.

It is preferred that compound of formula (1a") is itaconic acid, acrylic acid or an anhydride thereof, most preferably acrylic acid and the intramolecular anhydride of itaconic acid.

Alternatively or additionally to the first polymerizable monomer comprising at least one optionally protected carboxylic acid group, which preferably is in the form of compound of formula (1a), one or more first polymerizable monomer(s) may be provided in (i) of step a), preferably in the form of first polymerizable monomer(s) comprising at least one optionally protected acidic group selected from the group consisting of a phosphoric acid ester group, a phosphonic acid group and a sulfonic acid group.

Preferably, first polymerizable monomer(s) comprising an optionally protected phosphoric acid ester group and a first polymerizable organic moiety have the following formula (1b):

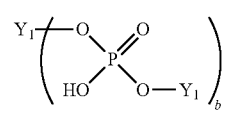

wherein the moieties $Y_1$ independent from each other represent a hydrogen atom or a moiety of the following formulae ($Y_1$*), ($Y_1$) or ($Y_1$*):

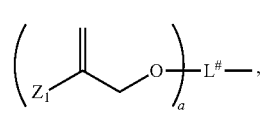

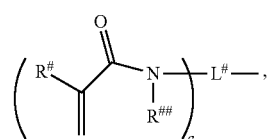

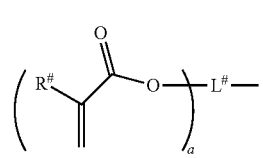

wherein $Z_1$ is $COOR^°$, $COSR^\square$, $CON(R^°)_2$, $CONR^°R^\square$, or $CONHR^°$, wherein $R^°$ and $R^\square$ independently represent a hydrogen atom, a linear $C_{1-18}$ or branched $C_{3-18}$ alkyl group optionally substituted by a $C_{3-8}$ cycloalkyl group, an optionally substituted $C_{3-8}$ cycloalkyl group, an optionally substituted $C_{4-18}$ aryl or heteroaryl group, an optionally substituted $C_{5-18}$ alkylaryl or alkylheteroaryl group, or an optionally substituted $C_{7-30}$ aralkyl group, whereby two $R^{20}$ residues may form together with the adjacent nitrogen atom to which they are bound a 5- to 7-membered heterocyclic ring which may contain further nitrogen atoms or an oxygen atoms, and whereby the optionally substituted groups may be substituted by 1 to 5 $C_{1-5}$ alkyl group(s);

$R^{\#}$ and $R^{\#\#\#}$ independently represent a hydrogen atom, an optionally substituted linear $C_{1-18}$ or branched $C_{3-18}$ alkyl group, an optionally substituted $C_{3-18}$ cycloalkyl group, an optionally substituted $C_{5-18}$ aryl or heteroaryl group, an optionally substituted $C_{5-18}$ alkylaryl or alkylheteroaryl group, an optionally substituted $C_{7-30}$ aralkyl group, whereby the optionally substituted groups may be substituted by 1 to 5 $C_{1-5}$ alkyl group(s);

L represents an (a+b)-valent organic residue (whereby b is 1 when Y in formula (1b) is within the round brackets) containing 2 to 45 carbon atoms and optionally heteroatoms such as oxygen, nitrogen and sulfur atoms, the carbon atoms including a+b carbon atoms selected from primary and secondary aliphatic carbon atoms, secondary alicyclic carbon atoms, and aromatic carbon atoms, each of said a+b carbon atoms linking a phosphate or a moiety of any one of formulae (Y*), (Y) or (Y*); a is an integer of from 1 to 10, preferably 1 to 5; b is an integer of from 1 to 10, preferably 1 to 5; provided that at least one Y is not hydrogen. The preparation of such compounds wherein Y=Y* is known from EP-A 1 548 021.

Most preferred are compounds of formula (1b) having a single first polymerizable organic moiety, that is a is 1.

First polymerizable monomer(s) comprising an optionally protected phosphonic acid group and a first polymerizable organic moiety have the following formula (1c):

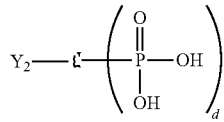

(1c)

wherein
the moiety $Y_2$ represents a moiety of the following formulae ($Y_2$*), ($Y_2$) or ($Y_2$*):

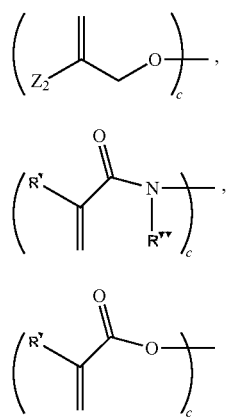

($Y_2$*)

($Y_2$**)

($Y_2$***)

$Z_2$ independently has the same meaning as defined for $Z_1$;

$R^{\blacktriangledown}$ and $R^{\blacktriangledown\blacktriangledown}$ independently have the same meaning as defined for $R^{\#}$ and $R^{\#\#}$;

$L^{\blacktriangledown}$ represents a (c+d) valent organic residue containing 2 to 45 carbon atoms and optionally heteroatoms such as oxygen, nitrogen and sulfur, the carbon atoms including c+d carbon atoms selected from primary and secondary aliphatic carbon atoms, secondary alicyclic carbon atoms, and aromatic carbon atoms, each of said c+d carbon atoms linking a phosphonate or a moiety of any one of formulae ($Y_2$*), ($Y_2$) or ($Y_2$*); and c and d independently represent integers of from 1 to 10.

Most preferred are compounds of formula (1c) having a single first polymerizable organic moiety, that is c is 1.

Preferably, first polymerizable monomer(s) comprising an optionally protected sulfonic acid group and a first polymerizable organic moiety have the following formula (1d):

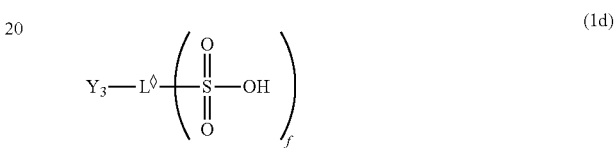

(1d)

wherein
the moiety $Y_3$ represents a moiety of the following formulae ($Y_3$*), ($Y_3$) or ($Y_3$*):

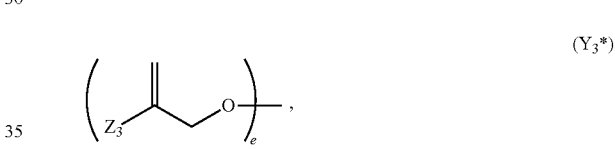

($Y_3$*)

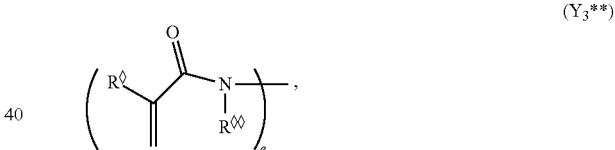

($Y_3$**)

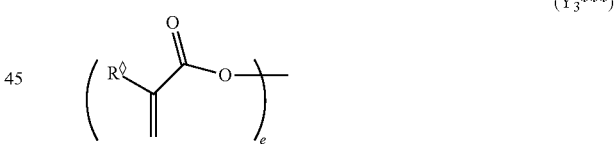

($Y_3$***)

$Z_3$ independently has the same meaning as defined for $Z_1$;
$R^{\diamond}$ and $R^{\diamond\diamond}$ independently have the same meaning as defined for $R^{\#}$ and $R^{\#\#}$;
wherein
$Z_2$ independently has the same meaning as defined for $Z_1$;
$L^{\diamond}$ represents an (e+f) valent organic residue containing 2 to 45 carbon atoms and optionally heteroatoms such as oxygen, nitrogen and sulfur atoms, the carbon atoms including e+f carbon atoms selected from primary and secondary aliphatic carbon atoms, secondary alicyclic carbon atoms, and aromatic carbon atoms, each of said e+f carbon atoms linking a sulphonate or a moiety of any one of formulae ($Y_3$*), ($Y_3$) or ($Y_3$*); and
e and f independently represent an integer of from 1 to 10.

Most preferred are compounds of formula (1d) having a single first polymerizable organic moiety, that is e is 1.

From the first polymerizable monomer comprising at least one optionally protected phosphoric acid ester group and at least one polymerizable organic moiety, compounds of formula (1b') characterized by one of the following formulae are particularly preferred:

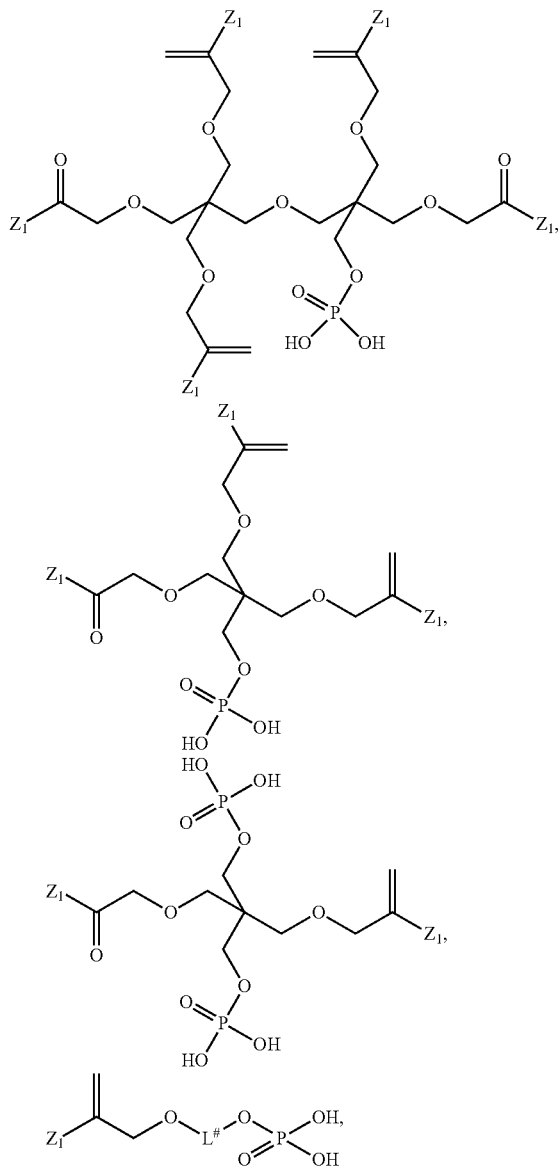

and most preferred are compounds of formula (1d) having the following formula:

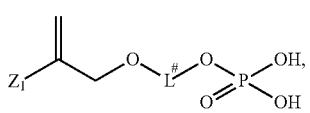

wherein $Z_1$ is defined as above, and $L^\#$ is an optionally substituted alkylene group. More preferably, $Z_1$ is methyl, and $L^\#$ is an unsubstituted alkylene group. Even more preferably, $L^\#$ is linear or branched $C_4$ to $C_{16}$ alkylene, yet even more preferably linear or branched $C_8$ to $C_{12}$ alkylene, and in particular linear or branched $C_{10}$ alkylene (decylene), most preferably linear $C_{10}$ alkylene.

From the first polymerizable monomer comprising at least one optionally protected phosphonic acid group and at least one polymerizable organic moiety, compounds of formula (1d') characterized by one of the following formulae are particularly preferred:

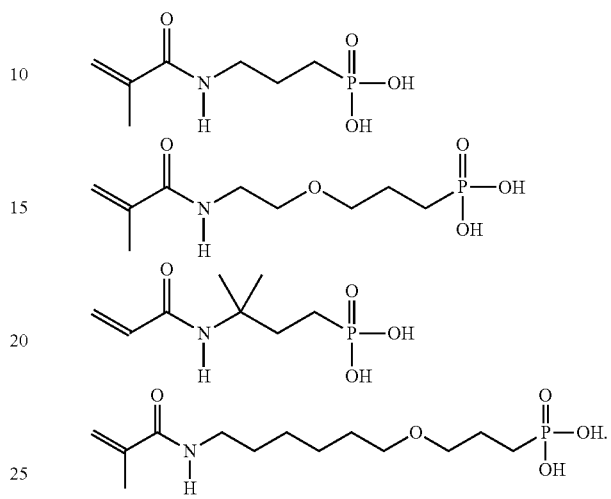

From the first polymerizable monomer comprising at least one optionally protected sulfonic acid group and at least one polymerizable organic moiety, compounds of formula (1e') characterized by one of the following formulae are particularly preferred:

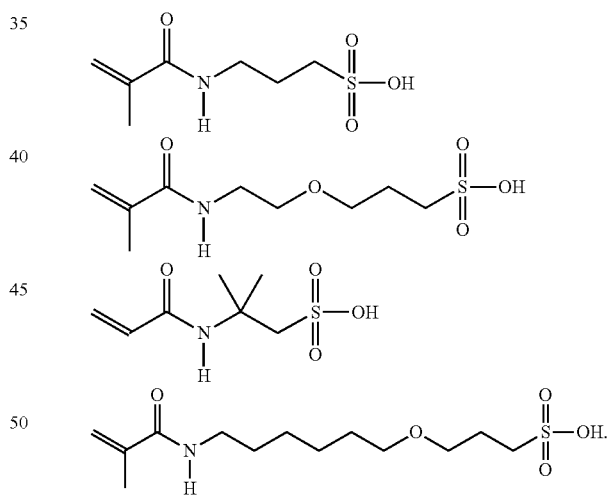

The optional second copolymerizable monomer is represented by the general formula (2):

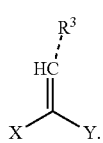

(2)

In formula (2), $R^3$ is a hydrogen atom or a linear $C_{1-6}$ or branched or cyclic $C_{3-8}$ alkyl group which may be substituted with a —COOZ' group. Preferably, R³ is a hydrogen atom. In formula (2), the dotted line indicates that R³ may be in either the cis or trans orientation relative to moiety X.

In formula (2), X is a protected hydroxyl or amino group, or a hydrocarbon group having 1 to 20 carbon atoms, which is substituted with a hydroxyl group and/or an amino group which may carry a protecting group, wherein the hydrocarbon group may contain 1 to 6 heteroatoms, which heteroatoms are selected from an oxygen atom, nitrogen atom, and sulfur atom, and/or which hydrocarbon group may contain a group selected from an amide bond or a urethane bond and which hydrocarbon group may further be substituted with up to 6 groups selected from —COOZ', amino groups, hydroxyl groups and thiol groups.

In X of formula (2), the hydrocarbon group having 1 to 20 carbon atoms may be a linear $C_{1-20}$ or branched or cyclic $C_{3-20}$ alkyl group, or a $C_{6-20}$ aryl group.

Preferably, X is a hydrocarbon group having 1 to 20 carbon atoms, which is substituted with an hydroxyl group and/or amino group which may carry a protecting group, wherein the hydrocarbon group may contain a heteroatom, which heteroatom is selected from an oxygen atom and a nitrogen atom, and/or which hydrocarbon group may contain a group selected from an amide bond or a urethane bond and which hydrocarbon group may further be substituted with a —COOZ' group. More preferably, X is a hydrocarbon group having 1 to 20 carbon atoms, even more preferably 1 to 6 carbon atoms, which is substituted with an hydroxyl group and/or amino group which may carry a protecting group, wherein the hydrocarbon group may contain an oxygen atom and/or which hydrocarbon group may contain an amide bond and which hydrocarbon group may further be substituted with a —COOZ' group. In a specific embodiment wherein X is a protected hydroxyl group, the compound of formula (2) is preferably a formyl alcohol, wherein the hydroxyl group carries a protecting group in the form of an formyl group.

The protecting group of a(n) (optionally) protected hydroxyl and/or amino group is not particularly limited and may be any conventional protecting group for a hydroxyl group or an amino group as, for example, described in P. G. M. Wuts and T. W. Greene, Greene's Protective Groups in Organic Synthesis, 4th Edition, John Wiley and Sons Inc., 2007.

Preferably, the hydroxyl-protecting group is selected from the group consisting of alkyl, alkenyl, benzyl, benzoyl, methoxymethyl (MOM), tetrahydropyranyl (THP), tert-butyldimethylsilyl (TBDMS), tert-butyldiphenylsilyl (TB-DPS), acetyl, pivalalyl. More preferably, the hydroxyl-protecting group is selected from the group consisting of C1-6 alkyl, C2-6 alkenyl, benzyl, benzoyl, acetyl and pivalyl. Most preferably, the hydroxyl-protecting group is selected from the group consisting of tert-butyl, benzyl, benzoyl, formyl, acetyl and pivalyl.

Further, hydroxyl-protecting groups having a polymerizable organic moiety, such as vinyl or allyl, may also be selected. However, if a hydroxyl-protecting group having a polymerizable organic moiety is selected, it is preferred to remove this hydroxyl-protecting group in a water-soluble polymer comprising acidic groups obtained by steps a) and optionally b) in order to obtain a water-soluble polymer comprising acidic groups according to (B). Because, it is particularly preferred that the water-soluble polymer comprising acidic groups according to (B) is a non-polymerizable polymer having no polymerizable organic moiety, specifically no polymerizable double bond.

Preferably, the amino-protecting group is selected from the group consisting of an acyl group, an arylalkyl group, an alkoxy carbonyl group, and an aryloxycarbonyl group. More preferably, the amino-protecting group is an acyl group. Most preferably, the amino-protecting group is a formyl group.

In formula (2), Y is a hydrogen atom, a —COOZ' group, or a hydrocarbon group having 1 to 20 carbon atoms, wherein the hydrocarbon group may contain 1 to 6 heteroatoms, which heteroatoms are selected from an oxygen atom, nitrogen atom, and sulfur atom, and/or which hydrocarbon group may contain a group selected from an amide bond or a urethane bond and which hydrocarbon group may further be substituted with up to 6 groups selected from —COOZ', amino groups, hydroxyl groups and thiol groups. Preferably, Y is a hydrogen atom, a —COOZ' group, or a hydrocarbon group having 1 to 20 carbon atoms, wherein the hydrocarbon group may contain a heteroatom, which heteroatom is selected from an oxygen atom and a nitrogen atom, and/or which hydrocarbon group may contain a group selected from an amide bond or a urethane bond and which hydrocarbon group may further be substituted with a —COOZ' group. More preferably, Y is a hydrogen atom or a hydrocarbon group having 1 to 20 carbon atoms, even more preferably 1 to 6 carbon atoms, wherein the hydrocarbon group may contain an oxygen atom and/or which hydrocarbon group may contain an amide bond and which hydrocarbon group may further be substituted with a —COOZ' group. In one embodiment, Y is a hydrogen atom.

In Y of formula (2), the hydrocarbon group having 1 to 20 carbon atoms may be a linear $C_{1-20}$ or branched or cyclic $C_{3-20}$ alkyl group, or a $C_{6-20}$ aryl group.

In formula (2), Z' which may be the same or different, independently represents a hydrogen atom, a metal ion, a protecting group for a carboxylic acid group, or the forms with a further —COOZ' group present in the molecule an intramolecular anhydride group. In one embodiment, Z' is a protecting group for a carboxylic acid group. In another embodiment, Z' is a hydrogen atom. The metal ion may be a monovalent metal ion such as an alkali metal ion. In another embodiment, Z' is a hydrogen atom. When Z forms with a further —COOZ' group present in the molecule an intramolecular anhydride group (—C(O)OC(O)—).

In an embodiment, Z' is a hydrogen atom and the polymerization reaction is conducted in an alkaline environment. In an alternative embodiment, Z' is a hydrogen atom and the hydroxyl groups of the second copolymerizable monomer carry a protecting group.

Preferred structures are exemplified in Scheme 1 below wherein a hydroxyl group may also carry a protecting group.

Scheme 1

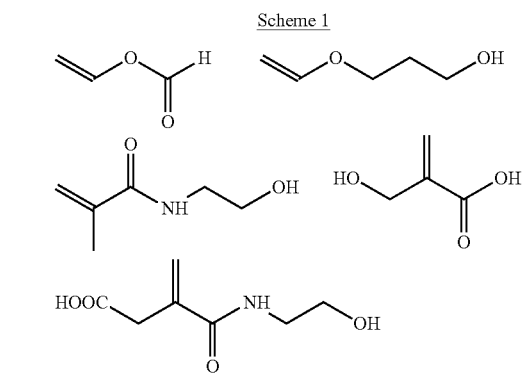

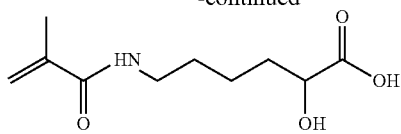

Preferably, the optional amino-protecting group is selected from an acyl group, an arylalkyl group, an alkoxy carbonyl group, and an aryloxycarbonyl group. More preferably, the amino-protecting group is an acyl group. Most preferably, the amino-protecting group is a formyl group.

Preferably, the second copolymerizable monomer comprising one or more optionally protected amino groups is selected from allyl amine, aminopropyl vinyl ether, aminoethyl vinyl ether, N-vinyl formamide and 2-aminomethyl acrylic acid. In an embodiment, the second copolymerizable monomer is aminopropyl vinyl ether. The amino group may be in the form of an ammonium salt such as a ammonium chloride.

Preferred structures wherein the amino group may also carry a protecting group are depicted in Scheme 2 below.

Scheme 2

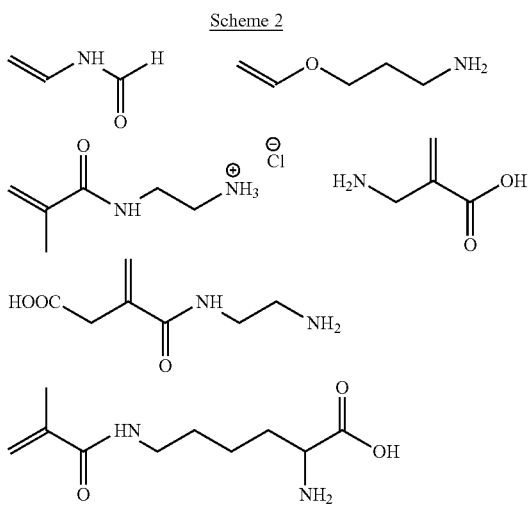

Preferably, the second copolymerizable monomer is represented by the general formula (2'):

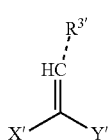

(2')

wherein
$R^{3'}$ is a hydrogen atom;
X' is a protected hydroxyl or amino group, or a hydrocarbon group having 1 to 6 carbon atoms, which is substituted with a hydroxyl group and/or an amino group which may carry a protecting group and which hydrocarbon group may further be substituted with a —COOH group;
Y' is a hydrogen atom, a —COOH group or a hydrocarbon group having 1 to 6 carbon atoms, which hydrocarbon group may further be substituted with a —COOH group.

More preferably, the second copolymerizable monomer is represented by the general formula (2"):

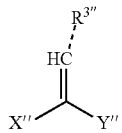

(2")

wherein
$R^{3''}$ is a hydrogen atom;
X" is a protected hydroxyl or amino group, or a hydrocarbon group having 1 to 3 carbon atoms, which is substituted with a hydroxyl group and/or an amino group which may carry a protecting group, which hydrocarbon group may contain an amide bond and which hydrocarbon group may further be substituted with a —COOH group;
Y" is a hydrogen atom, a —COOH group or a hydrocarbon group having 1 to 3 carbon atoms, which hydrocarbon group may further be substituted with a —COOH group.

If X, X' and X" of formulae (2), (2') and (2") is a hydrocarbon group substituted with a hydroxyl group and an amino group, then it is preferred that either the hydroxyl group or the amino group is protected, or both hydroxyl and amino group are protected with protecting groups which preferably can be selectively removed under different conditions.

Preferably, in formulae (2), (2') and (2"), X, X' and X" respectively is a protected hydroxyl or amino group or a hydrocarbon group as defined in formulae (2), (2') and (2") above, which hydrocarbon group is substituted with a hydroxyl group or an amino group which may carry a protecting group.

More preferably, in formulae (2), (2') and (2"), X, X' and X" respectively is a protected hydroxyl group or a hydrocarbon group as defined in formulae (2), (2') and (2") above, which hydrocarbon group is substituted with a hydroxyl group which may carry a protecting group.

The molar ratio of first polymerizable monomer to second copolymerizable monomer in the mixture copolymerized in step a) (mol first polymerizable monomer/mol second copolymerizable monomer) is preferably in the range of from 100:1 to 100:50, more preferably in the range from 100:2 to 100:20, still more preferably in a range from 100:3 to 100:10.

The further copolymerizable monomers optionally to be used in step a) comprise at least one, preferably one to three, more preferably one or two, most preferably one optionally protected acidic group(s) which are not carboxylic acid groups. Specific examples of acidic groups are sulfonic acid groups (—SO$_3$M), phosphonic acid groups (—PO$_3$M$_2$) or phosphoric acid ester groups (—OPO$_3$M$_2$), or salts thereof, wherein M may independently be a hydrogen atom or a monovalent ion such as an alkali metal or an ammonium ion.

Specific examples of the optional further monomers are selected from 2-acrylamido-2-methylpropane sulfonic acid, vinyl phosphonate, and vinyl sulfonic acid.

Step a) of the aqueous dental glass ionomer composition proceeds as a chain-growth polymerization. In case in (i) of step a), two different first polymerizable monomers are polymerized, or optionally (ii) is applied, radical copolymerization proceeds, whereby a water-soluble copolymer is obtained.

The type of copolymer formed by step a) of the present disclosure may be a statistical copolymer, a random copolymer, an alternating copolymer, a block copolymer or a combination thereof.

For example, a copolymer obtained by step a) comprising (ii) is an optionally protected hydroxyl group containing copolymer, such as, for example, a copolymer obtainable by copolymerization of an acrylate and an anhydride of (meth)acrylic acid or a derivative thereof.

The reaction conditions of the polymerization reaction according to step a) of the present disclosure are not particularly limited. Accordingly, it is possible to carry out the reaction in the presence or absence of a solvent. A suitable solvent may be selected from the group of water, dimethyl formamide (DMF), tetrahydrofurane (THF), and dioxane.

The reaction temperature is not particularly limited. Preferably, the reaction is carried out at a temperature of between −10° C. to the boiling point of the solvent. Preferably, the reaction temperature is in the range of from 0° C. to 80° C.

The reaction time is not particularly limited. Preferably the reaction time is in the range of from 10 minutes to 48 hours, more preferably 1 hour to 36 hours.

The reaction is preferably carried out in the presence of a polymerization initiator. In an embodiment of the aqueous dental glass ionomer composition, the polymerization initiator is selected from azobisisobutyronitrile (AIBN), 2,2-azobis(2-amidinopropane)dihydrochloride, 2,2'-azobis(2-methylbutyronitrile), 2,2'-azobis(N,N'-dimethyleneisobutyramidine) dihydrochloride, and 4,4'-azobis(4-cyano pentanoic acid). The amount of the polymerization initiator is not particularly limited. Suitably, the amount is in the range of from 0.001 to 5 mol % based on the total amount of the monomers.

It is preferred that in step (i) and optionally (ii), the obtained water-soluble polymer comprising acidic groups does not comprise pendant β-dicarbonyl group(s).

The reaction product obtained in step a) may be isolated by precipitation and filtration, or lyophilization. The product may be purified according to conventional methods.

Step b) of the aqueous dental glass ionomer composition is an optional step of coupling a compound having a functional group reactive with an acidic group of repeating units derived from the first polymerizable monomer and/or a functional group reactive with hydroxyl group of repeating units derived from the second copolymerizable monomer to the water-soluble polymer comprising acidic groups obtained in step a), wherein the optionally protected carboxylic acid or hydroxyl group is deprotected.

The optional coupling reaction in step b) is a condensation reaction or an addition reaction forming a linking group selected from an ester or urethane group.

The term "functional group reactive with optionally protected acidic group of repeating units derived from the first polymerizable monomer or a hydroxyl group of repeating units derived from the second copolymerizable monomer in the water-soluble polymer obtained in step a)" as used herein means any group which can form a covalent bond with a carboxyl or hydroxyl group of the water-soluble polymer comprising acidic groups according to (B).

If one or more of the carboxyl and optional hydroxyl groups of repeating units derived from the first polymerizable monomer and second copolymerizable monomer in the water-soluble (co)polymer obtained in step a) is protected, the at least one or more carboxyl and optional hydroxyl group can be deprotected prior to step b) or concomitant with step b).

The conditions for deprotection of an optionally protected carboxyl or hydroxyl group are selected according to the protecting group used. Preferably, the protected carboxyl or hydroxyl group is deprotected by hydrogenolysis or treatment with acid or base.

(C) The Water-Soluble, Hydrolysis-Stable Monomer Having a Single Polymerizable Double Bond The aqueous dental glass ionomer composition according to the present disclosure comprises a water-soluble, hydrolysis-stable monomer having a single polymerizable double bond and optionally a carboxylic acid group or hydroxyl group. According to (C), the monomer having a single polymerizable double bond is water-soluble and hydrolysis-stable.

The term "hydrolysis-stable" used in this connection means that the monomer according to (C) is stable to hydrolysis in an acidic medium, such as in a dental composition. In particular, the monomer according to (C) does not contain groups such as ester groups, and does not hydrolyze in aqueous solution at pH 3 at room temperature within one month.

The monomer according to (C) polymerizes in the presence of the crosslinker according to (D) and the polymerization initiator system according to (E). A monomer according to (C) has a single polymerizable double bond. Suitable polymerizable double bonds are carbon-carbon double bonds such as alkenyl groups and vinyl groups.

In an embodiment of the aqueous dental glass ionomer composition, the water-soluble, hydrolysis-stable monomer according to (C) is a compound represented by the general formula (3):

(3)

wherein $A^\#$ is a single bond or a linear $C_{1-15}$ or branched or cyclic $C_{3-15}$ alkylene group, wherein if the carbon number of the alkylene group is two or more, then the alkylene group may contain 1 to 3 heteroatoms, wherein each heteroatom is located in between two carbon atoms of the alkylene carbon chain, which heteroatoms are selected from an oxygen atom, nitrogen atom, and sulfur atom, and/or which alkylene group may contain, if its carbon number is two or more, in between two carbon atoms of the alkylene carbon chain 1 to 3 groups selected from an amide bond or a urethane bond.

In formula (3), the jagged line indicates that $R^4$ may be in either the cis or trans orientation relative to the moiety -$A^\#$—CO-$G^\#$.

Preferably, $A^\#$ is a single bond, a linear $C_{1-15}$ or branched or cyclic $C_{3-15}$ alkylene group or a —CO-[Het-$C_{1-5}$ alkylene]$_n$- group wherein Het is a secondary amino group (NH) or an oxygen atom with n=1 to 3, and wherein $C_{1-5}$ alkylene includes linear $C_{1-5}$ or branched $C_{3-5}$ alkylene. Most preferably, $A^\#$ represents a single bond, a methylene or ethylene group or a —CO-Het-$C_{1-3}$ alkylene group.

Further, in formula (3), $R^4$ is a hydrogen atom, a —COO$Z^\#$ group, or a linear $C_{1-6}$ or branched or cyclic $C_{3-8}$ alkyl group which may be substituted with a —COO$Z^\#$ group. $Z^\#$ which may be the same or different, independently represents a hydrogen atom, a metal ion, a protecting group for a carboxylic acid group, or the $Z^\#$ forms with a further —COO$Z^\#$ group present in the molecule an intramolecular anhydride group.

$R^5$ represents a hydrogen atom, —OM*, —COOM, a linear $C_1$ to $C_{18}$ and branched $C_3$ to $C_{18}$ alkyl group which may be substituted with a $C_{3-6}$ cycloalkyl group, a $C_{6-14}$ aryl or $C_{3-14}$ heteroaryl group, —OM*, —COOM, —PO$_3$M, —O—PO$_3$M$_2$ or —SO$_3$M, a $C_3$ to $C_{18}$ cycloalkyl group which may be substituted with a $C_{1-16}$ alkyl group, a $C_{6-14}$ aryl or $C_{3-14}$ heteroaryl group, —OM*, —COOM, —PO$_3$M, —O—PO$_3$M$_2$ or —SO$_3$M, or a $C_5$ to $C_{18}$ aryl or $C_3$ to $C_{18}$ heteroaryl group which may be substituted with —OM*, —COOM, —PO$_3$M, —O—PO$_3$M$_2$ or —SO$_3$M.

Further, in formula (3), $G^{\#}$ is —OH or —NR$_6$R*$_6$, wherein R$_6$ and R*$_6$ independently represent a hydrogen atom, a linear $C_1$ to $C_{18}$ or branched $C_3$ to $C_{18}$ alkyl group which may be substituted with a $C_{3-6}$ cycloalkyl group, a $C_{6-14}$ aryl or $C_{3-14}$ heteroaryl group, —OM*, —COOM, —PO$_3$M, —O—PO$_3$M$_2$ or —SO$_3$M, a $C_3$ to $C_{18}$ cycloalkyl group which may be substituted with a $C_{1-16}$ alkyl group, a $C_{6-14}$ aryl or $C_{3-14}$ heteroaryl group, —OM*, —COOM, —PO$_3$M, —O—PO$_3$M$_2$ or —SO$_3$M, or a $C_5$ to $C_{18}$ aryl or $C_3$ to $C_{18}$ heteroaryl group which may be substituted with —OM*, —COOM, —PO$_3$M, —O—PO$_3$M$_2$ or —SO$_3$M, wherein R$_6$ and R*$_6$ may cooperatively form a ring in which R$_6$ and R*$_6$ may be linked by a C—C bond or a functional group which may be selected from the group consisting of an ether group, a thioether group, an amine group and an amide group.

M* of $R^5$, R$_6$ and R*$_6$ are independent from each other, each represents a hydrogen atom or a hydroxyl-protecting group, and M of any one $R^5$, R$_6$ and R*$_6$ are independent from each other, each represents a hydrogen atom, a carboxyl-protecting group or a metal atom. The hydroxyl-protecting group M* may be one as described above for the second polymer, and the carboxyl-protecting group M may be one as described above for the first polymerizable monomer.

Preferably, in case R$_6$ and R*$_6$ cooperatively form a ring, a 3 to 10 membered ring is formed, more preferably a 5 to 7 membered ring.

For $R^5$, the linear $C_1$ to $C_{18}$ and branched $C_3$ to $C_{18}$ alkyl group may e.g. be methyl, ethyl, n-propyl, i-propyl, n-butyl, isobutyl, tert-butyl, sec-butyl, pentyl or hexyl. For R$_6$ and R*$_6$, the $C_{1-18}$ alk(en)yl group may e.g. be eth(en)yl, n-prop(en)yl, i-prop(en)yl, n-but(en)yl, isobut(en)yl, tert-but(en)yl sec-but(en)yl, pent(en)yl or hex(en)yl.

For $R^5$, R$_6$ and R*$_6$, an aryl group may, for example, be a phenyl group or a naphthyl group, and a $C_{3-14}$ heteroaryl group may contain 1 to 3 heteroatoms selected from nitrogen, oxygen and sulfur.

Preferably, in formula (3), $R^5$ represents a hydrogen atom, —COOM, a linear $C_{1-16}$ or branched $C_{3-16}$ alkyl group which may be substituted with a $C_{3-6}$ cycloalkyl group, a $C_{6-14}$ aryl or $C_{3-14}$ heteroaryl group, —OM*, or COOM, a $C_{3-6}$ cycloalkyl group which may be substituted with a linear $C_{1-16}$ or branched $C_{3-16}$ alkyl group, a $C_{6-14}$ aryl or $C_{3-14}$ heteroaryl group, —OM* or —COOM, a $C_{6-14}$ aryl or $C_{3-14}$ heteroaryl group, —OM* or —COOM, a $C_{6-14}$ aryl or $C_{3-14}$ heteroaryl group which may be substituted with —OM*, or —COOM.

Preferably, in formula (3), R$_6$ and R*$_6$ independently represent a hydrogen atom, a linear $C_{1-16}$ or branched $C_{3-16}$ alkyl group which may be substituted with a $C_{3-6}$ cycloalkyl group, a $C_{6-14}$ aryl or $C_{3-14}$ heteroaryl group, —OM* or —COOM, a $C_{3-6}$ cycloalkyl group which may be substituted with a linear $C_{1-16}$ or branched $C_{3-16}$ alkyl group, a $C_{6-14}$ aryl or $C_{3-14}$ heteroaryl group, —OM* or —COOM, a $C_{6-14}$ aryl or $C_{3-14}$ heteroaryl group which may be substituted with —OM* or —COOM. More preferably, R$_6$ and R*$_6$ independently represent a hydrogen atom, a linear $C_{1-10}$ or branched $C_{3-10}$ alkyl group which may be substituted with a $C_{4-6}$ cycloalkyl group, a $C_{6-10}$ aryl or $C_{4-10}$ heteroaryl group, a $C_{4-6}$ cycloalkyl group which may be substituted with a $C_{1-6}$ alkyl group, a $C_{6-10}$ aryl or $C_{4-10}$ heteroaryl group, or a $C_{6-10}$ aryl group, wherein R$_6$ and R*$_6$ may cooperatively form a ring in which R$_6$ and R*$_6$ may be linked by a C—C bond or a functional group which may be selected from the group consisting of an ether group, a thioether group, an amine group and an amide group. Even more preferably, R$_6$ and R*$_6$ independently represent a hydrogen atom, a linear $C_{1-10}$ or branched $C_{3-10}$ alkyl group which may be substituted with a $C_{6-10}$ aryl group or —OH, a cyclic $C_{3-10}$ alkyl group which may be substituted with —OH, or R$_6$" and R*$_6$" independently represent a linear $C_{1-10}$ or branched $C_{3-10}$ alkyl group which cooperatively form a ring in which R$_6$" and R*$_6$" are linked by a C—C bond or an ether group. Yet even more preferably, R$_6$ and R*$_6$ represent a linear $C_{1-6}$ or branched $C_{3-6}$ alkyl group which may be substituted with a $C_{6-10}$ aryl group or —OH, a cyclic $C_{3-6}$ alkyl group, or R$_6$" and R*$_6$" independently represent a linear $C_{1-6}$ or branched $C_{3-6}$ alkyl group which cooperatively form a ring in which R$_6$" and R*$_6$" are linked by a C—C bond or an ether group. Still even more preferably, R$_6$ and R*$_6$ independently represent a methyl group, an ethyl group, a 2-hydroxyethyl group, a n-propyl group, a benzyl group, an α-methylbenzyl group, a cyclohexyl group and an adamantyl group. Most preferably, R$_6$ and R*$_6$ independently represent a methyl or ethyl group.

Preferably, the monomer according to (C) is a compound according to formula (3) wherein $A^{\#}$ represents a single bond, that is a (meth)acryl compound. Most preferably, the monomer according to (C) is a compound according to formula (3) wherein $A^{\#}$ represents a single bond and $G^{\#}$ is —NR$_6$R*$_6$, that is a (meth)acrylamide compound.

Monomers according to (C) comprising a carboxylic acid group are particularly advantageous, since such monomers introduce additional carboxylic acid groups into the acidic polymer in the aqueous dental glass ionomer composition, which can undergo a cement reaction resulting in a further improved setting or curing reaction in the presence of the reactive particulate glass according to (A).

Preferably, the water-soluble, hydrolysis-stable monomer of formula (3") is a (meth)acrylamide compound selected from the group consisting of:

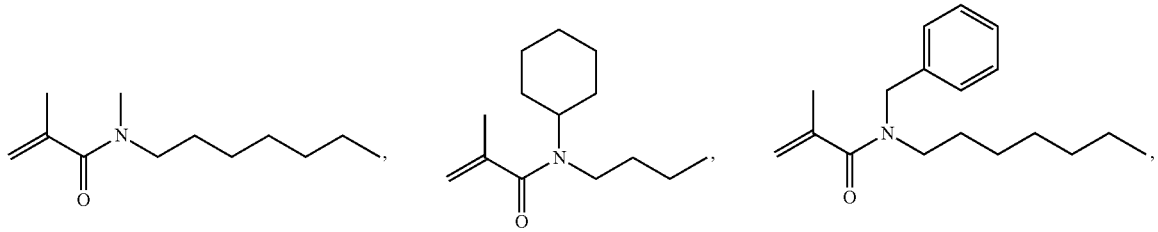

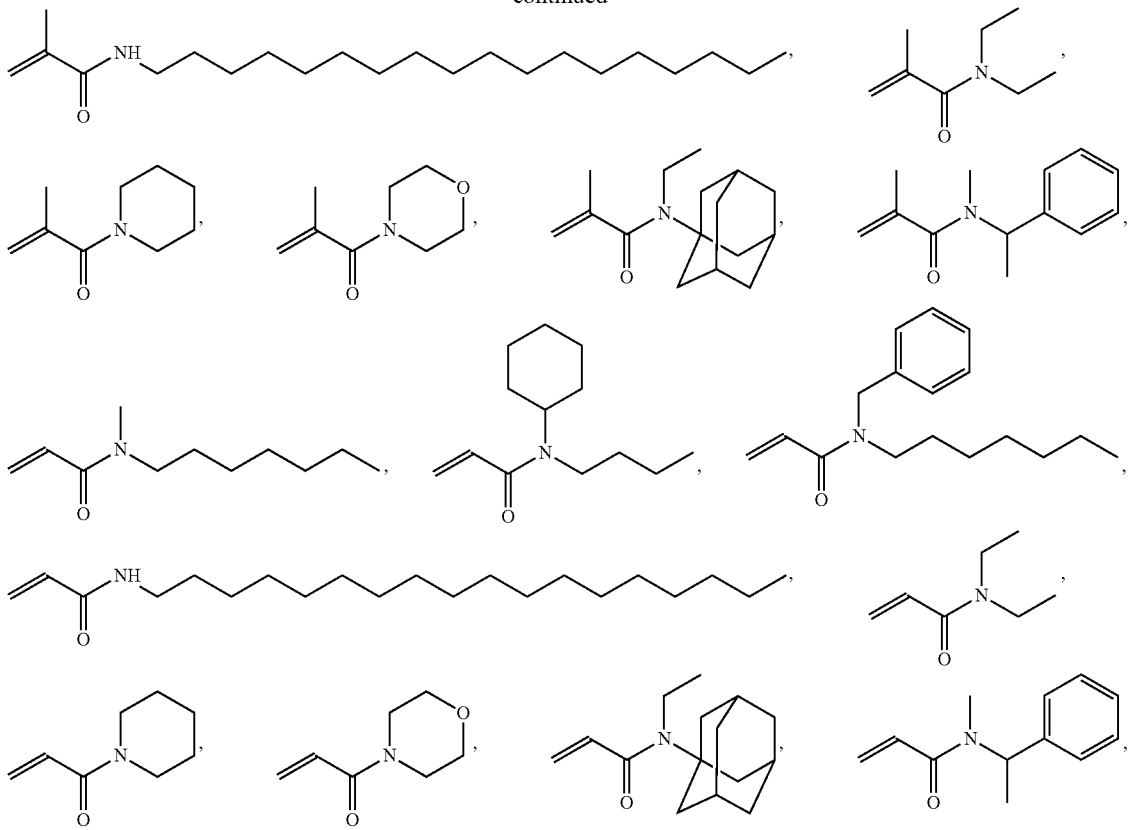

2-hydroxyethyl acrylamide (HEAA), N,N-dimethyl(meth)acrylamide, N,N-di-n-propyl(meth)acrylamide, and N-ethyl-N-methyl(meth)acrylamide.

Most preferably, the water-soluble, hydrolysis-stable monomer compound of formula (3″) is selected from the group consisting of 2-hydroxyethyl acrylamide (HEAA), N,N-dimethyl(meth)acrylamide, N,N-diethyl(meth)acrylamide, N,N-di-n-propyl(meth)acrylamide, and N-ethyl-N-methyl(meth)acrylamide.

Preferably, in the monomer according to (C) of formula (3), residues $R^5 R_6$ and $R^*_6$ are selected with the proviso that the molecular weight of the monomer having a single polymerizable double bond according to (C) is at most 600 Da, preferably at most 400 Da, more preferably at most 200 Da, even more preferably at most 150 Da, most preferably at most 120 Da.

The monomer according to (C) is preferably selected in view of a good processability and applicability of the final aqueous dental glass ionomer composition, in particular in terms of viscosity. Therefore, the viscosity of the monomer according to (C) is preferably in the range of 0.1 to 100 mPa·s, more preferably 0.3 to 50 mPa·s, even more preferably 0.5 to 25 mPa·s, yet even more preferably 0.8 to 10 mPa·s, in particular 0.9 to 3 mPa·s.

Preferably, the monomer according to (C) is contained in the aqueous dental glass ionomer composition in an amount of from 0.1 to 40, more preferably 1 to 32 even more preferably 5 to 28, most preferably 8 to 20 percent by weight based on the total weight of the aqueous dental glass ionomer composition. When the monomer according to (C) is absent, a long-term mechanical resistance may be low. On the other hand, when the amount monomer according to (C) exceeds 40 percent of weight, shrinkage of the dental glass ionomer cement obtained from the present aqueous dental glass ionomer composition may occur. Specifically, by limiting the amount of monomer according to (C) to 20 percent of weight of the aqueous dental glass ionomer composition or less, shrinkage of the dental glass ionomer cement obtained from the present aqueous dental glass ionomer composition can particularly effectively be avoided.

(D) The Polymerizable Crosslinker Having at Least Two Polymerizable C—C Double Bonds The aqueous dental glass ionomer composition according to the present disclosure comprises a water-soluble, hydrolysis-stable polymerizable crosslinker having at least two polymerizable carbon-carbon double bonds.

The polymerizable crosslinker according to (D) is hydrolysis-stable, which means that the crosslinker is stable to hydrolysis in an acidic medium, such as in a dental composition.

Specifically, the crosslinker does not contain groups such as ester groups, and does not hydrolyze in aqueous solution at pH 3 at room temperature within one month.

The crosslinker according to (D) may be an alkylenediol dimethylacrylate such as 1,3-butanediol dimethacrylate, 1,4-butanediol dimethacrylate, an alkylenediol divinyl ether such as 1,4-butanediol divinyl ether, di(ethylene glycol) dimethacrylate, di(ethylene glycol) divinyl ether, pentaerythritol diacrylate monostearate, ethylene glycol dimethacrylate, trimetylolpropane trimethacrylate, pentaerythritol triacrylate or triallyl ether, pentaerythritol tetraacrylate and trimetylolpropane triacrylate.

However, preferred is a crosslinker in the form of a polymerizable compound of the following formula (4), which is disclosed in patent publications EP2705827, WO2014040729 and in patent application EP 15 178 515:

$$A''\text{-}L(B)_{n'} \quad (4)$$

wherein
A'' is a group of the following formula (5)

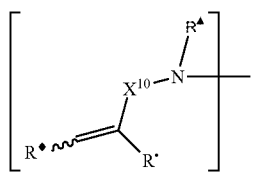
(5)

$X^{10}$ is CO, CS, CH$_2$, or a group $[X^{100}Z^{10}]_k$, wherein $X^{100}$ is an oxygen atom, a sulfur atom or NH, $Z^{10}$ is a linear $C_{1-4}$ or branched or cyclic $C_{3-6}$ alkylene group, and k is an integer of from 1 to 10;

R$^\blacklozenge$ is a hydrogen atom,
—COOM$^{10}$,
a linear $C_{1-16}$ or branched $C_{3-16}$ alkyl group which may be substituted with a $C_{3-6}$ cycloalkyl group, a $C_{6-14}$ aryl or $C_{3-14}$ heteroaryl group, —COOM$^{10}$, —PO$_3$M$^{10}$, —O—PO$_3$M$^{10}{}_2$ or —SO$_3$M$^{10}$,
a $C_{3-6}$ cycloalkyl group which may be substituted with a linear $C_{1-16}$ or branched $C_{3-16}$ alkyl group, a $C_{6-14}$ aryl or $C_{3-14}$ heteroaryl group, —COOM$^{10}$, —PO$_3$M$^{10}$, —O—PO$_3$M$^{10}{}_2$ or —SO$_3$M$^{10}$,
a $C_{6-14}$ aryl or $C_{3-14}$ heteroaryl group which may be substituted with —COOM$^{10}$, —PO$_3$M$^{10}$, —O—PO$_3$M$^{10}{}_2$ or —SO$_3$M$^{10}$, R$^\bullet$ is a hydrogen atom,
—COOM$^{10}$
a linear $C_{1-16}$ or branched $C_{3-16}$ alkyl group which may be substituted with a $C_{6-14}$ aryl or $C_{3-14}$ heteroaryl group, —COOM$^{10}$, —PO$_3$M$^{10}$, —O—PO$_3$M$^{10}{}_2$ and —SO$_3$M$^{10}$,
a $C_{3-6}$ cycloalkyl group which may be substituted with a linear $C_{1-16}$ or branched $C_{3-16}$ alkyl group, a $C_{6-14}$ aryl or $C_{3-14}$ heteroaryl group, —COOM$^{10}$, —PO$_3$M$^{10}$, —O—PO$_3$M$^{10}{}_2$ or —SO$_3$M$^{10}$, or
a $C_{6-14}$ aryl or $C_{3-14}$ heteroaryl group which may be substituted with —COOM$^{10}$, —PO$_3$M$^{10}$, —O—PO$_3$M$^{10}{}_2$ and —SO$_3$M$^{10}$, R$^\blacktriangle$ is a hydrogen atom,
a linear $C_{1-16}$ or branched $C_{3-16}$ alkyl or linear $C_{2-16}$ or branched $C_{3-16}$ alkenyl group which may be substituted with a $C_{3-6}$ cycloalkyl group, a $C_{6-14}$ aryl or $C_{3-14}$ heteroaryl group, —COOM$^{10}$, —PO$_3$M$^{10}$, —O—PO$_3$M$^{10}{}_2$ or —SO$_3$M$^{10}$, a $C_{3-6}$ cycloalkyl or cycloalkenyl group which may be substituted with a $C_{1-16}$ alkyl group, a $C_{6-14}$ aryl or $C_{3-14}$ heteroaryl group, —COOM$^{10}$, —PO$_3$M$^{10}$, —O—PO$_3$M$^{10}{}_2$ or —SO$_3$M$^{10}$, a $C_{6-14}$ aryl group which may be substituted with —COOM$^{10}$, —PO$_3$M$^{10}$, —O—PO$_3$M$^{10}{}_2$ or —SO$_3$M$^{10}$, preferably R$^\blacktriangle$ is a linear $C_{1-10}$ or branched $C_{3-10}$ alkyl or linear $C_{2-10}$ or branched $C_{3-10}$ alkenyl group which may be substituted with a $C_{4-6}$ cycloalkyl group, a $C_{6-10}$ aryl or $C_{6-10}$ heteroaryl group, more preferably R$^\blacktriangle$ is a linear $C_{1-6}$ or branched $C_{3-6}$ alkyl or alkenyl group which may be substituted with a $C_{6-10}$ aryl, most preferably R$^\blacktriangle$ is a methyl group, an ethyl group, an allyl group or a benzyl group, most preferably an ethyl group or an allyl group, L is a single bond or a linker group;
B is selected from:
(i) a group according to the definition of A'',
(ii) a group of the following formula (6)

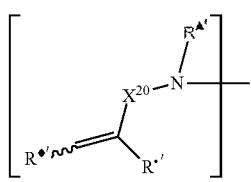
(6)

wherein
$X^{20}$ independently has the same meaning as defined for $X^1$ in formula (5),
R$^{\blacklozenge\prime}$ and R$^{\bullet\prime}$ are independent from each other and independently have the same meaning as defined for R$^\blacklozenge$ and R$^\bullet$ of formula (5),
R$^{\blacktriangle\prime}$ is a hydrogen atom,
a linear $C_{1-16}$ or branched $C_{3-16}$ alkyl group which may be substituted with a $C_{3-6}$ cycloalkyl group, a $C_{6-14}$ aryl or $C_{3-14}$ heteroaryl group, —COOM$^{10}$, —PO$_3$M$^{10}$, —O—PO$_3$M$^{10}{}_2$ or —SO$_3$M$^{10}$,
a $C_{3-6}$ cycloalkyl group which may be substituted with a linear $C_{1-16}$ or branched $C_{3-16}$ alkyl group, a $C_{6-14}$ aryl or $C_{3-14}$ heteroaryl group, —COOM$^{10}$, —PO$_3$M$^{10}$, —O—PO$_3$M$^{10}{}_2$ or —SO$_3$M$^{10}$,
a $C_{6-14}$ aryl group which may be substituted with —COOM$^{10}$, —PO$_3$M$^{10}$, —O—PO$_3$M$^{10}{}_2$ or —SO$_3$M$^{10}$, (iii) a group of the following formula (IV)

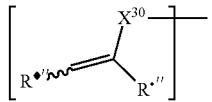
(7)

wherein
$X^{30}$ is CO, —CH$_2$CO—, CS, or —CH$_2$CS—,
R$^{\blacklozenge\prime\prime}$ and R$^{\bullet\prime\prime}$ which are independent from each other and independently have the same meaning as defined for R$^\blacklozenge$ and R$^\bullet$ of formula (5), or (iv) a group $[X^{40}Z^{200}]_p$E,
wherein
$Z^{200}$ is a linear $C_{1-4}$ or branched $C_{3-6}$ alkylene group,
$X^{40}$ is an oxygen atom, a sulfur atom or NH,
E is a hydrogen atom,
PO$_3$M$_2$,
a linear $C_{1-16}$ or branched $C_{3-16}$ alkyl group which may be substituted with a $C_{3-6}$ cycloalkyl group, a $C_{6-14}$ aryl or $C_{3-14}$ heteroaryl group, —COOM$^{10}$, —PO$_3$M$^{10}$, —O—PO$_3$M$^{10}{}_2$ or —SO$_3$M$^{10}$,
a $C_{3-6}$ cycloalkyl group which may be substituted with a linear $C_{1-16}$ or branched $C_{3-16}$ alkyl group, a $C_{6-14}$ aryl or $C_{3-14}$ heteroaryl group, —COOM$^{10}$, —PO$_3$M$^{10}$, —O—PO$_3$M$^{10}{}_2$ or —SO$_3$M$^{10}$, a $C_{6-14}$ aryl or $C_{3-14}$ heteroaryl group which may be substituted with —COOM$^{10}$, —PO$_3$M$^{10}$, —O—PO$_3$M$^{10}{}_2$ or —SO$_3$M$^{10}$, and p is an integer of from 1 to 10;

and n' is an integer of from 1 to 4;

wherein M$^{10}$ which are independent from each other each represent a hydrogen atom or a metal atom.

In formulae (5), (6) and (7), the jagged line indicates that R$^\blacklozenge$, R$^{\blacklozenge\prime}$ and R$^{\blacklozenge\prime\prime}$ may be in either the cis or trans orientation relative to X$^{10}$, X$^{20}$ or X$^{30}$.

Preferably, when L is a single bond in formula (4), B cannot be a group according to the definition of A" or a group of the formula (6).

The following groups are preferred groups of formula (5), wherein M is a hydrogen atom or a metal atom:

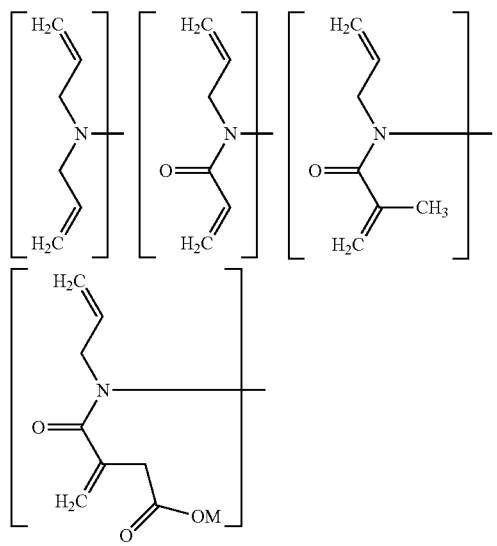

For L, the linker group may be a hydrocarbon group which may be aliphatic and/or aromatic and preferably has 1 to 45 carbon atoms. The hydrocarbon group may be substituted with 1 to 6 $C_{1-4}$ alkyl groups. Specific examples of the alkyl groups are methyl, ethyl, n-propyl, propyl, n-butyl, i-butyl or tert.-butyl. In an embodiment, for L, the hydrocarbon group of the linker group may contain 1 to 5 heteroatoms selected from oxygen, nitrogen and sulphur. The oxygen atoms and sulphur atoms in the hydrocarbon group may be in the form of ether or thioether bonds, keto or sulfoxide groups, carboxylic acid or ester groups, sulfonic acid or ester groups, hydroxyl groups and thiol or thioester groups. In case of an aliphatic group, L may be a linear $C_1$ to $C_{18}$ or branched $C_3$ to $C_{18}$ alkylene group, linear $C_2$ to $C_{18}$ and branched $C_3$ to $C_{18}$ alkenylene group, $C_3$ to $C_{18}$ cycloalkylene or cycloalkenylene group. In case of an aromatic group, L may be a $C_6$ to $C_{18}$ arylene or a heteroarylene group comprising 6 to 18 carbon atoms. Specifically, L may be a divalent substituted or unsubstituted linear $C_1$ to $C_{20}$ or branched $C_3$ to $C_{20}$ alkylene group, substituted or unsubstituted $C_{6-14}$ arylene group, substituted or unsubstituted $C_3$ to $C_{20}$ cycloalkylene group, substituted or unsubstituted $C_7$ to $C_{20}$ arylenealkylene group.

According to one embodiment, L represents a saturated or unsaturated aliphatic $C_{2-20}$ hydrocarbon chain which may contain 2 to 4 oxygen atoms or nitrogen atoms, and which may be substituted with 1 to 6 linear $C_{1-4}$ or branched or cyclic $C_{3-8}$ alkyl groups, or L may be a substituted or unsubstituted $C_7$ to $C_{20}$ arylenealkylene group which may be substituted with 1 to 6 linear $C_{1-4}$ or branched or cyclic $C_{3-6}$ alkyl groups.

Preferably, the linker group is a divalent $C_{1-12}$ hydrocarbon group. The divalent $C_{1-12}$ hydrocarbon group may contain 1 to 3 carbonyl groups or heteroatoms selected from oxygen, nitrogen and sulfur. Moreover, the $C_{1-12}$ hydrocarbon group may be substituted with a hydroxyl group, a $C_{6-14}$ aryl group, —COOM, —PO$_3$M, —O—PO$_3$M$_2$ or —SO$_3$M, wherein M is a hydrogen atom or a metal atom. Specific examples of a divalent $C_{1-12}$ hydrocarbon group are linear $C_{1-12}$ or branched or cyclic $C_{3-12}$ alkylene groups such as a methylene, ethylene, propylene or butylene group, and linear $C_{2-12}$ or branched $C_{3-12}$ alkenylene groups such as a ethenylene, propenylene or butenylene group, which groups may be substituted with a hydroxyl group, a $C_{6-14}$ aryl group, —COOM, —PO$_3$M, —O—PO$_3$M$_2$ or —SO$_3$M.

Preferred divalent linker groups may be selected from methylene, ethylene, propylene, butylene, ethenylene, propenylene (prop-1-enylene or prop-2-enylene) or butenylene (but-1-enylene, but-2-enylene) and the following divalent groups:

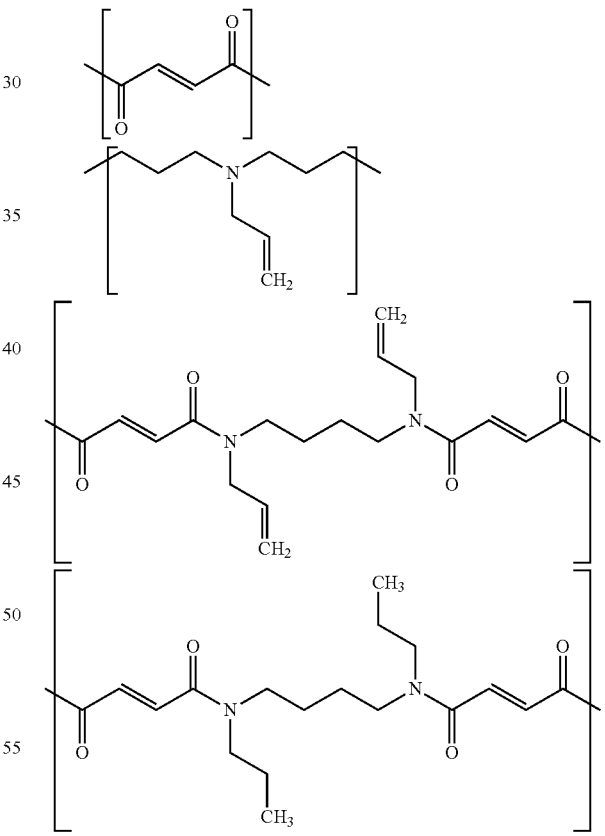

Preferably, in the crosslinker of formula (4), X$^{10}$ is CO, that is, the crosslinker is a (meth)acrylamide compound.

More preferably, the crosslinker of formula (4) is selected from the group consisting of 1,3-bisacrylamido-propan (BAP), 1,3-bisacrylamido-2-ethyl-propan (BAPEN), N,N-di(allyl acrylamido) propane and compounds having the following structural formulae:

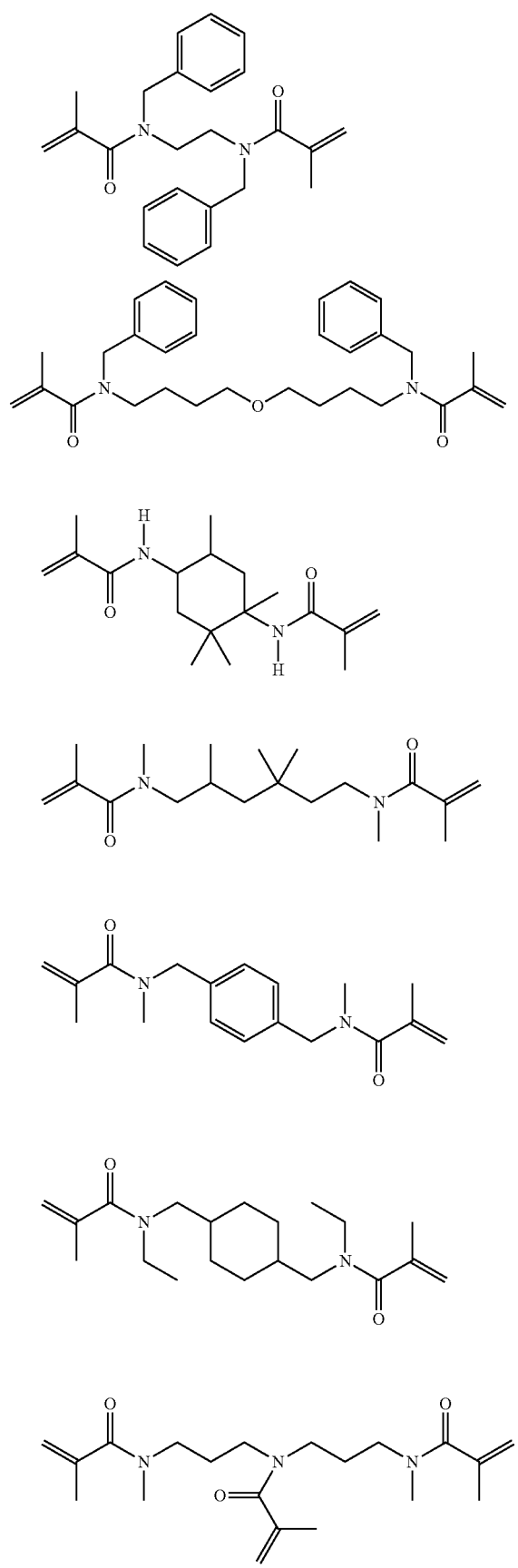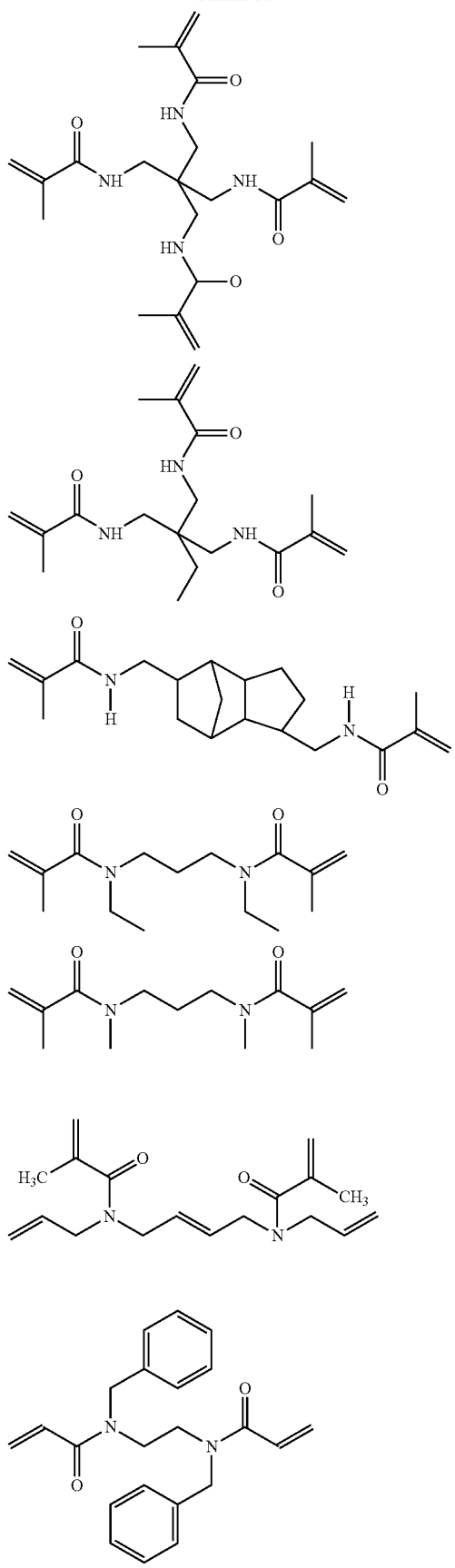

-continued

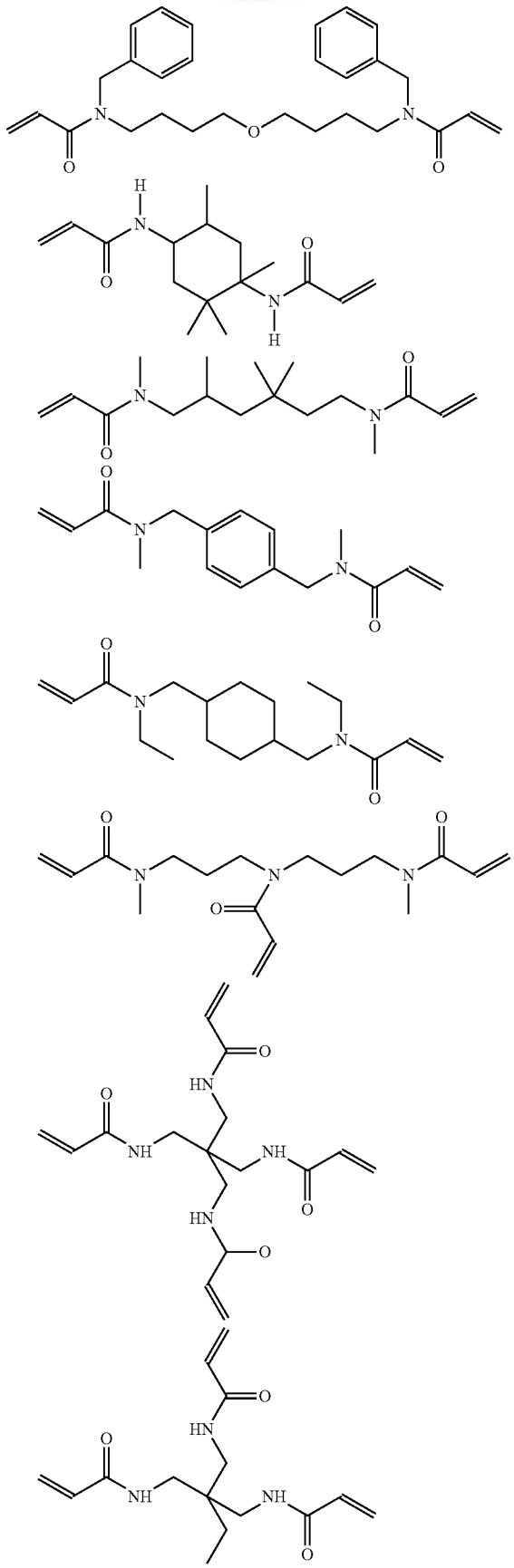

-continued

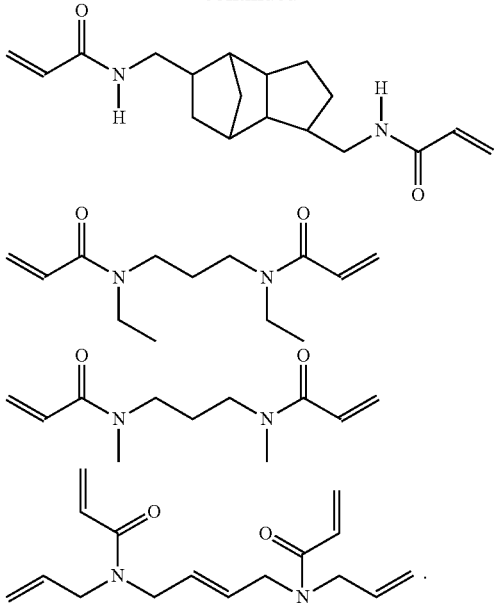

Even more preferably, the crosslinker of formula (4) is selected from the group consisting of N,N'-(2E)-but-2-en-1,4-diallylbis-[N-prop-2-en-1) amide (BAABE), N,N'-diethyl-1,3-bisacrylamido-propan (BADEP), 1,3-bisacrylamido-propan (BAP), 1,3-bisacrylamido-2-ethyl-propan (BAPEN) and N,N-di(allyl acrylamido) propane. Most preferably, compound of formula (4) is N,N'-(2E)-but-2-en-1,4-diallylbis-[(N-prop-2-en-1) amide (BAABE) or N,N'-diethyl-1,3-bisacrylamido-propan (BADEP).

It is preferred that the crosslinker is a macromonomer of the following formula (8):

$$AX_n \quad (8)$$

The macromonomer of formula (8) comprises a moiety A, and at least one substituent X.

In formula (8), A is a straight chain, branched and/or cyclic linker group containing at least n nitrogen atoms, whereby the linker group A has polyoxyalkylene and/or polyalkylene imine repeating units and optionally one or more acidic groups. The linker group A has a valency of at least one which corresponds to the total number of substituents X. Accordingly, linker group A may be preferably monovalent (n=1), divalent (n=2), trivalent (n=3), tetravalent (n=4), pentavalent (n=5), or hexavalent (n=6). Preferably, linker group A is divalent or trivalent, most preferably divalent.

Preferably, the linker group A may be a straight chain, branched and/or cyclic monomeric, oligomeric, polymeric or copolymeric group containing nitrogen atoms at the terminal positions for forming an amide bond with a moiety X. A monomeric groups is a low-molecular group having a molecular weight of up to 500. An oligomeric group is a group having a molecular weight of more than 500 to up to 10000 and may be prepared by a polymerization reaction.

According to a further embodiment, the polymerizable compound of formula (8) contains one or more acidic groups selected from carboxylic acid groups, phosphonic acid groups, sulfonic acid groups or phosphoric acid ester groups.

In formula (8), X are moieties containing a polymerizable double bond and forming an amide bond with a nitrogen atom of A, which X may be the same or different and are represented by the following formula (9).

(9)

In formula (9), the waved bond is attached to the nitrogen atoms of at least two of the termini of formula (10).

In formula (9), $R^7$ and $R^8$ are independent from each other and represent a hydrogen atom, a linear $C_{1-6}$ or branched or cyclic $C_{3-8}$ alkyl group or a group $—(CH_2)_m—COOM$, wherein M is a hydrogen atom or a metal atom and m is an integer of from 0 to 6. The metal atom may be an alkali metal atom or an alkaline earth metal. In case of an alkaline earth metal, the second charge on the metal atom is neutralized by either a further carboxylic acid anion or another anion. Preferably, $R^7$ is a hydrogen atom or a methyl group. Preferably, $R^8$ is a hydrogen atom or a group $—(CH_2)_m—COOH$, wherein m is 0, 1 or 2, most preferably $R^8$ is a hydrogen atom.

In formula (9), L* is a bond or a linear $C_{1-6}$ or branched or cyclic $C_{3-8}$ alkylene group, preferably a single bond or a methylene or ethylene group. Most preferably, in formula (9), L* is a single bond, that is the macromonomer of formula (8) is a (meth)acrylamide macromonomer.

Preferably, in formula (8), n is an integer of at least one, preferably 2 to 4, most preferably 2.

Preferably, in formula (8), A is a linker group represented by the following formula (10), wherein the nitrogen atom of at least two of the termini forms an amide bond with a substitutent X:

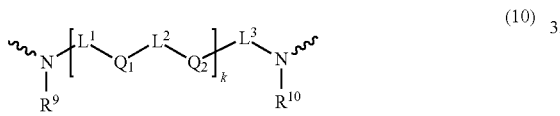

(10)

In formula (10), the waved bonds are respectively attached to a carbonyl moiety of formula (9).

In formula (10), $R^9$ and $R^{10}$ independently represent a hydrogen atom or a substituted or unsubstituted aliphatic or cycloaliphatic hydrocarbon group. Substituents of the aliphatic or cycloaliphatic hydrocarbon group may be selected from hydroxyl groups, thiol groups, amino groups, or carboxylic acid groups or a salt thereof. $R^9$ and $R^{10}$ may be the same or different. According to an embodiment, $R^9$ and $R^{10}$ independently represent a hydrogen atom or a lower alkyl group having 1 to 6 carbon atoms, more preferably 1 to 3 carbon atoms.

In formula (10), $L^1$, $L^2$, and $L^3$ may be the same or different. In case a plurality of $L^1$ an $L^2$ are present when k is at least 2, each of $L^1$ and $L^2$ may be the same or different. Preferably, each of $L^1$ and each of the plurality $L^2$ are the same. $L^1$, $L^2$, and $L^3$ independently represent a single bond, or a linear $C_{2-20}$ or branched or cyclic $C_{3-20}$ hydrocarbon group containing from 1 to 6 heteroatoms selected from nitrogen and oxygen in the backbone of the hydrocarbon group, and optionally from 1 to 6 functional groups selected from carboxylic acid groups or a salt thereof, hydroxyl groups, thiol groups and amino groups. In a particular embodiment, $L_1$, $L_2$, and $L_3$ do not carry an optional functional group.

Preferably, at least one, more preferably at least two of $L_1$, $L_2$, and $L_3$, do not represent a single bond. Preferably, $L_1$, $L_2$, and $L_3$ contain 1 or 2 heteroatoms selected from nitrogen, and oxygen in the backbone of the hydrocarbon group. Preferably, the hydrocarbon group has 1 to 6 carbon atoms and contains 1 or 2 heteroatoms selected from nitrogen, and oxygen in the backbone of the hydrocarbon group, and optionally from 1 to 3 carboxylic acid groups or a salt thereof.

In formula (10), $Q_1$ and $Q_2$, may be the same or different. $Q_1$ and $Q_2$ may represent a single bond or a linkage selected from an amide, a urethane, a urea and a thiourea linkage. Preferably, at least one of $Q_1$ and $Q_2$ is not a single bond. In case $Q_1$ and $Q_2$ represent an amide or urethane linkage, the orientation of the amide or urethane linkage may be the same or different.

In formula (10), k is an integer of at least 0. When k is 0, then $L_3$ cannot be a single bond. Preferably, k is in the range of from 0 to 60, more preferably from 1 to 40, even more preferably from 3 to 20, and most preferably from 5 to 10.

The linker group A imparts water solubility to the compound of formula (8). Water solubility within the sense of the present disclosure means that the compound of formula (8) can be dissolved as a 0.1 percent by weight solution in water at 25° C. Preferably, the compound of formula (8) of the present disclosure has a water solubility of at least 2.0 weight % in water at 25° C.

Preferably, the crosslinker in the form of the macromonomer of formula (8) is a (meth)acrylamide compound having the following structural formula:

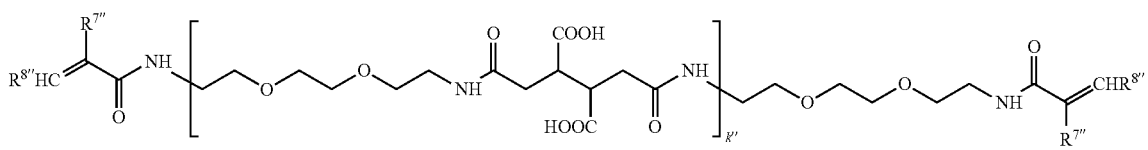

wherein
$R^{7''}$ is a hydrogen atom or a methyl group and
$R^{8''}$ is a hydrogen atom or a group $—(CH_2)_m—COOH$, wherein m is 0, 1 or 2, most preferably $R^{16''}$ and $R^{17''}$ are a hydrogen atom, and
k" is from 3 to 20, most preferably from 5 to 10.

For example, the macromonomer of formula (8) may be prepared by a process comprising (i) a step of a step-growth polymerization including a condensation reaction or addition reaction of a mixture containing a polyamine having a moiety of the following formula (11) and additional hydrogen atoms, and a compound of the following formula (12) having at least two carboxylic acid groups, said carboxylic acid groups may be present in the form of an anhydride in the presence of a compound of the following formula (13).

The polyamine of formula (11) has the following structural formula:

(11)

wherein $R^{\alpha}$ represents an y-valent $C_{2-20}$ straight-chain, branched or cyclic hydrocarbon group which may optionally contain from 1 to 6 heteroatoms selected from nitrogen, oxygen, or sulphur atoms in the backbone of the hydrocarbon group, and optionally from 1 to 6 functional groups selected from hydroxyl groups, thiol groups and amino groups;

$R^{\beta}$ represents a hydrogen atom or a substituted or unsubstituted aliphatic or cycloaliphatic hydrocarbon group; and y represents an integer of at least 2.

The compound of formula (12) having at least two carboxylic acid groups has the following structural formula:

$$MOOC-R^{\gamma}-COOM \quad (12)$$

wherein $R^{\gamma}$ represents a linear $C_{1-20}$ or branched, cyclic $C_{3-20}$ or aromatic $C_{6-20}$ hydrocarbon group which may optionally contain from 1 to 6 heteroatoms selected from nitrogen, oxygen, or sulphur atoms in the backbone of the hydrocarbon group, and optionally from 1 to 6 functional groups selected from carboxylic acid groups, hydroxyl groups, thiol groups and amino groups, wherein the M which may be the same or different independently represent a hydrogen atom or a metal atom. The metal atom may be an alkali metal or an alkali earth metal. In case of an alkali earth metal, the additional charge on the metal may be neutralized by a further carboxylic acid anion or another anion present in the system.

The compound of formula (13) has the following structure:

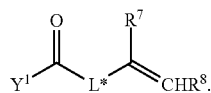
(13)

In compound of formula (13), L*, $R^7$ and $R^8$ are defined as above, and $Y^1$ is a leaving group, preferably a leaving group in the form of a chlorine or bromine atom, or $Y^1$ forms an intramolecular anhydride group together with a carboxylic acid group present in $R^7$ or $R^8$ and the adjacent carbonyl group.

The addition or condensation reaction may form part of a step-growth polymerization step.

The process further may further comprise a step (ii) of introducing the moieties of the formula (10) by reacting the polyamide obtained in step (i) with a compound of formula (12) wherein $Y^1$ is a leaving group and $R^7$ and $R^8$ are as defined above; or a step (iii) of reacting a mixture containing a polyamine of formula (11), a compound of formula (12) and a compound of formula (14) for obtaining an amide.

The process may also comprise a step of a step-growth polymerization of a mixture containing the amide obtained in (iii) and a compound having at least two carboxylic acid groups or an anhydride thereof for obtaining the water-soluble polymerizable compound of the formula (1).

Most preferably, the aqueous dental glass ionomer composition according to the present disclosure comprises a combination of one or more crosslinkers of formula (8) and one or more crosslinkers of formula (4).

Preferably, the water-soluble, hydrolysis stable polymerizable crosslinker according to (D) is contained in an amount of from 1 to 45 percent by weight, more preferably 5 to 30 percent by weight, most preferable 10 to 20 percent by weight based on the total weight of the aqueous dental glass ionomer composition.

(E) The Polymerization Initiator System

The aqueous dental glass ionomer composition according to the present disclosure comprises a polymerization initiator system. As a polymerization initiator system according to (E), any compound or system capable of initiating the copolymerization reaction according to the present disclosure may be used. The polymerization initiator according to (E) may be a photoinitiator or a redox initiator or a mixture thereof.

A suitable redox initiator comprises reducing and oxidizing agents, which produce free-radicals capable of initiating polymerization of polymerizable double bonds in components (C) and (D) independent from the presence of light. The reducing and oxidizing agents are selected so that the polymerization initiator system is sufficiently storage-stable and free of undesirable colorization to permit storage and use under typical dental conditions. Moreover, the reducing and oxidizing agents are selected so that the polymerization initiator system is sufficiently miscible with the resin system to permit dissolution of the polymerization initiator system in the composition.

Useful reducing agents include ascorbic acid, ascorbic acid derivatives, and metal complexed ascorbic acid compounds as described in U.S. Pat. No. 5,501,727; amines, namely tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine, salts of a dithionite or sulfite anion, and mixtures thereof.

Suitable oxidizing agents include persulfuric acid and salts thereof, such as ammonium, sodium, potassium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof. One or more different oxidizing agents or one or more different reducing agent may be used in the polymerization initiator system. Small quantities of transition metal compounds may also be added to accelerate the rate of redox cure. The reducing and oxidizing agents are present in amounts sufficient to permit an adequate free-radical reaction rate.

The reducing or oxidizing agents may be microencapsulated for enhancing shelf stability of the composition, and if necessary permitting packaging the reducing and oxidizing agents together (U.S. Pat. No. 5,154,762). Appropriate selection of an encapsulant may allow combination of the oxidizing and reducing agents and even of an acid-functional component and optional filler in a storage-stable state. Moreover, appropriate selection of a water-insoluble encapsulant allows combination of the reducing and oxidizing agents with the particulate reactive glass and water in a storage-stable state.

Suitable photoinitiators for polymerizing free radically photopolymerizable compositions may include binary and tertiary systems. Binary systems may include a photosensitizer and an electron donor compound, and tertiary photoinitiators may include an iodonium salt, a photosensitizer, and an electron donor compound as described in U.S. Pat. No. 5,545,676. Suitable iodonium salts include the diaryl iodonium salts, e.g., diphenyliodonium chloride, diphenyliodonium hexafluorophosphate, diphenyl-iodonium tetrafluoroborate, and tolylcumyliodonium tetrakis (pentafluorophenyl)borate. Suitable photosensitizers are monoketones and diketones that absorb some light within a range of about 400 nm to about 520 nm (preferably, about 450 nm to about 500 nm). Particularly suitable compounds include alpha diketones that have some light absorption within a range of about 400 nm to about 520 nm (even more preferably, about 450 to about 500 nm). Examples include camphorquinone, benzil, furil, 3,3,6,6-tetramethylcyclohexanedione, phenanthraquinone, 1-phenyl-1,2-propanedione and other 1-aryl-2-alkyl-1,2-ethanediones, and cyclic alpha diketones. Suitable electron donor compounds include substituted amines, e.g., ethyl dimethylaminobenzoate or dimethylamino benzonitrile.

Suitable photoinitiators may also include phosphine oxides typically having a functional wavelength range of about 380 nm to about 1200 nm. Examples of phosphine oxide free radical initiators with a functional wavelength range of about 380 nm to about 450 nm include acyl and bisacyl phosphine oxides such as those described in U.S. Pat. No. 4,298,738, 4,324,744 and 4,385,109 and EP 0 173 567. Specific examples of the acylphosphine oxides include 2,4,6-trimethylbenzoyldiphenylphosphine oxide, bis(2,4,6-trimethylbenzoyl)phenylphosphine oxide, dibenzoylphenylphosphine oxide, bis(2,6-dimethoxybenzoyl)phenylphosphine oxide, tris(2,4-dimethylbenzoyl)phosphine oxide, tris(2-methoxybenzoyl)phosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, benzoyl-bis(2,6-dimethylphenyl)phosphonate, and 2,4,6-trimethylbenzoylethoxyphenylphosphine oxide. Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819), bis(2,6-dimethoxybenzoyl)-(2,4,4-trimethylpentyl) phosphine oxide (CGI 403), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700), a 1:1 mixture, by weight, of bis(2,4,6-trimethylbenzoyl)phenyl phosphine oxide and 2-hydroxy-2-methyl-1-phenylpropane-1-one (DAROCUR 4265), and ethyl 2,4,6-trimethylbenzylphenyl phosphinate (LUCIRIN LR8893X). Typically, the phosphine oxide initiator is present in the composition in catalytically effective amounts, such as from 0.1 percent by weight to 5.0 percent by weight, based on the total weight of the composition.

Tertiary amine reducing agents may be used in combination with an acylphosphine oxide Examples of suitable aromatic tertiary amine include N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, N,N-bis(2-hydroxyethyl)-3,5-dimethylaniline, N,N-bis(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, 4-N,N-dimethylaminobenzoic acid ethyl ester, 4-N,N-dimethylaminobenzoic acid methyl ester, 4-N,N-dimethylaminobenzoic acid n-butoxyethyl ester, 4-N,N-dimethylaminobenzoic acid 2-(methacryloyloxy) ethyl ester, 4-N,N-dimethylaminobenzophenone ethyl 4-(N,N-dimethylamino) benzoate and N,N-dimethylaminoethyl methacrylate. Examples of an aliphatic tertiary amine include trimethylamine, triethylamine, N-methyldiethanolamine, N-ethyldiethanolamine, N-n-butyldiethanolamine, N-lauryldiethanolamine, triethanolamine, 2-(dimethylamino) ethyl methacrylate, N-methyldiethanolamine dimethacrylate, N-ethyldiethanolamine dimethacrylate, triethanolamine monomethacrylate, triethanolamine dimethacrylate, and triethanolamine trimethacrylate.

The amine reducing agent may be present in the composition in an amount from 0.1 percent by weight to 5.0 percent by weight, based on the total weight of the composition.

The amount of active species of the polymerization initiator is not particularly limited. Suitably, the amount of polymerization initiator in the polymerization system according to (E) is in the range of from 0.001 to 5 mol % based on the total amount of the monomers.

The Cured Aqueous Dental Glass Ionomer Composition

The present aqueous dental glass ionomer composition is a curable dental composition. A cured dental glass ionomer composition can be obtained by polymerizing the water-soluble, hydrolysis-stable monomer according to (C) and the water-soluble, hydrolysis-stable polymerizable crosslinker according to (D) in the presence of the reactive particulate glass (A), the water-soluble polymer comprising acidic groups according to (B) and the polymerization initiator system according to (E).

It was surprisingly found that when cured, the present dental glass ionomer composition has particularly advantageous mechanical properties:

The adhesive bond strength to dentin of the cured composition is at least 5 MPa as measured according to ISO 29022:2013; and The flexural strength of the cured composition is at least 50 MPa as measured according to ISO 4049.

(F) The Non-Reactive Filler

The present aqueous dental glass ionomer composition may further comprise (F) a non-reactive filler, which do not undergo a cement reaction with the polyacid polymer.

Non-reactive fillers may be included in the present aqueous dental glass composition for changing the appearance of the composition, for controlling viscosity of the composition, for further improving mechanical strength of a dental glass ionomer cement obtained from the composition, and e.g. for imparting radiopacity. The non-reactive filler should be non-toxic.

The filler may be an inorganic material. It can also be a crosslinked organic material or a composite material. For example, suitable non-reactive inorganic fillers may be quartz, nitrides such as silicon nitride, colloidal silica, submicron silica such as pyrogenic silicas, colloidal zirconia, feldspar, borosilicate glass, kaolin, talc or a metallic powder comprising one or more metals or metal alloys.

Examples of suitable non-reactive organic fillers include filled or unfilled particulate polycarbonates or polyepoxides. Preferably the surface of the non-reactive organic filler particles is treated with a coupling agent in order to enhance the bond between the filler and the matrix. Suitable coupling agents include silane compounds such as gamma-methacryloxypropyltrimethoxysilane, gamma-mercaptopropyltriethoxysilane and gamma-aminopropyltrimethoxysilane.

The non-reactive filler may have a unimodal or polymodal (e.g., bimodal) particle size distribution, wherein the particulate filler preferably has an average particle size of from 0.1 to 100 μm, preferably of from 1 to 40 μm. The particle size may be measured, for example, by electron microscopy or by using a conventional laser diffraction particle sizing method as embodied by a MALVERN Mastersizer S or MALVERN Mastersizer 2000 apparatus. The particulate filler may be a multimodal particulate non-reactive filler representing a mixture of two or more particulate fractions having different average particle sizes. The particulate reactive filler may also be a mixture of particles of different chemical composition. The particulate non-reactive filler may be surface modified by a surface modifying agent.

Further Optional Components

The aqueous dental glass ionomer composition according to the present disclosure may, besides of optional component (F), comprise additional optional components.

According to a specific embodiments, the aqueous dental glass ionomer composition does not comprise a polymerizable polymer having polymerizable double bond(s). According to a further specific embodiment, the aqueous dental glass ionomer composition does not comprise at least one of the following components: unmodified polyacrylic acid as water-soluble polymer according to (B), acrylic acid as water-soluble monomer according to (C) and/or NN-diethyl-1,3-bisacrylamido-propan (BADEP) as crosslinker according to (D).

For example, as additional optional components, the aqueous dental glass ionomer composition according to the present disclosure may also include further components to improve the radio-opacity, such as $CaWO_4$, $ZrO_2$, $YF_3$ or to increase the fluoride release such as $YF_3$.

Further, the aqueous dental glass ionomer composition according to the present disclosure may also include a modifying agent such as tartaric acid. Such modifying agent provides for adjusting the working time and a setting time of the glass ionomer cement reaction, respectively, when preparing the cement as described in U.S. Pat. No. 4,089,830, 4,209,434, 4,317,681 and 4,374,936. In general, an increase in working time results in an increase in setting time as well.

The "working time" is the time between the beginning of the setting reaction when the polymer and modified particulate reactive filler are combined in the presence of water, and the time the setting reaction proceeds to the point when it is no longer practical to perform further physical work upon the system, e.g. spatulate it or reshape it, for its intended dental or medical application.

The "setting time" is the time measured from the beginning of the setting reaction in a restoration to the time sufficient hardening has occurred to allow subsequent clinical or surgical procedures to be performed on the surface of the restoration.

In a setting reaction, due to the presence of polymerizable double bonds, a polymerization reaction takes place.

The aqueous dental glass ionomer composition according to the present disclosure may contain further components such as solvents, pigments, nonvitreous fillers, free radical scavengers, polymerization inhibitors, reactive and nonreactive diluents e.g. surfactants (such as to enhance solubility of an inhibitor e. g., polyoxyethylene), coupling agents to enhance reactivity of fillers e.g., 3-(trimethoxysilyl) propyl methacrylate, and rheology modifiers.

Suitable solvents or nonreactive diluents include alcohols such as ethanol and propanol.

Suitable reactive diluents are alpha,beta unsaturated monomers for providing altered properties such as toughness, adhesion, and set time. Such alpha,beta-unsaturated monomers may be acrylates and methacrylates such as methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate (HEMA), hydroxypropyl acrylate, hydroxypropyl methacrylate, tetrahydrofurfuryl acrylate, tetrahydrofurfuryl methacrylate, glycidyl acrylate, glycidyl methacrylate also termed bisphenol A glycerolate dimethacrylat ("bis-GMA", CAS-No. 1565-94-2), glycerol mono- and di-acrylate, glycerol mono- and di-methacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate (where the number of repeating ethylene oxide units vary from 2 to 30 especially triethylene glycol dimethacrylate ("TEGDMA"), neopentyl glycol diacrylate, neopentyiglycol dimethacrylate, trimethylolpropane triacrylate, trimethylol propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate, di-2-methacryloyloxethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethyl-hexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-metha-cryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl4-cyclohexyl carbamate, 2,2'-bis (4-methacryloxyphenyl)propane, 2,2'bis(4-acryloxyphenyl) propane, 2,2'-bis[4(2-hydroxy-3-methacryloxy-phenyl)] propane, 2,2'-bis[4(2-hydroxy-3-acryloxy-phenyl)propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl) propane, 2,2'-bis(4-acryloxydiethoxyphenyl)propane, 2,2'-bis[3(4-phenoxy)-2-hydroxypropane-1-methacrylate] propane, and 2,2'-bis[3(4-phenoxy)-2-hydroxypropane-1-acrylte]propane, may be mentioned. Other suitable examples of polymerizable components are isopropenyl oxazoline, vinyl azalactone, vinyl pyrrolidone, styrene, divinylbenzene, urethane acrylates or methacrylates, epoxy acrylates or methacrylates and polyol acrylates or methacrylates. Mixtures of alpha,beta-unsaturated monomers can be added if desired. Preferably, the mixed but unset dental compositions of the disclosure will contain a combined weight of about 0.5 to about 40%, more preferably about 1 to about 30%, and most preferably about 5 to 20% water, solvents, diluents and alpha,beta-unsaturated monomers, based on the total weight (including such water, solvents, diluents and alpha,beta-unsaturated monomers) of the mixed but unset aqueous dental glass ionomer compositioncomponents.

Examples of suitable free radical scavengers are 4-methoxyphenol, phenyl-N-tert-butylnitrone (PBN) and phenothiazine. An example of a suitable inhibitor is tert.-butyl hydroquinone (TBHQ), hydroxytoluene or butylated hydroxytoluene (BHT). The amount of inhibitor may be selected from 0.001 to 2% and preferably from 0.02 to 0.5% based on the total weight of the polymer according to (B)/monomer according to (C)/crosslinker according to (D)/water mixture.

Nanoparticles

Any particulate components of the present aqueous dental glass ionomer composition, such as the above described reactive particulate glass (A), non-reactive filler (F) or particulate further optional components may be in the form of nanoparticles.

The nanoparticles are preferably uniformly dispersed in the aqueous dental glass ionomer composition.

The nanoparticles may have an unimodal or polymodal (e.g., bimodal) particle size distribution.

It is preferred that the particles have diameters between 2 nm and 20 μm, more preferably between 2 nm and 200 nm.

Preferably, the aqueous dental glass ionomer composition comprises up to 80 percent by weight of dispersed nanoparticles, more preferably up to 75 percent based on the total weight of the composition.

Particular Embodiment of the Aqueous Dental Glass Ionomer Composition

According to a particular embodiment, the aqueous dental glass ionomer composition comprises (A) a reactive particulate glass comprising
 1) 20 to 45% by weight of silica,
 2) 20 to 40% by weight of alumina,
 3) 20 to 40% by weight of strontium oxide,
 4) 1 to 10% by weight of $P_2O_5$, and
 5) 3 to 25% by weight of fluoride;

(B) a water-soluble polymer comprising acidic groups, which is reactive with the particulate glass in a cement reaction, wherein the polymer is obtainable by a process comprising:
 a) a step of polymerizing a mixture comprising
  (i) a first polymerizable monomer represented by the general formula (1a'):

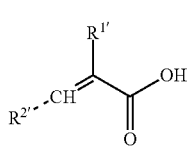

(1a')

wherein
 $R^{1'}$ is a hydrogen atom, or a linear $C_{1-4}$ or branched or cyclic $C_{3-6}$ alkyl group which may be substituted with a —COOH group,
 $R^{2'}$ is a hydrogen atom or a linear $C_{1-4}$ or branched or cyclic $C_{3-6}$ alkyl group which may be substituted with a —COOH group, preferably $R^{1'}$ and $R^{2'}$ are selected with the proviso that the molecular weight of the first polymerizable monomer is at most 200 Da, preferably at most 150 Da;
more preferably, the compound of formula (1') is selected from the group consisting of itaconic acid, (meth)acrylic acid, maleic acid or an anhydride thereof, more preferably compound of formula (1') is (meth)acrylic acid or the intramolecular anhydride of itaconic acid or maleic acid, most preferably, the compound of formula (1') is acrylic acid or the intramolecular anhydride of itaconic acid, and optionally
 (ii) a second copolymerizable monomer represented by the general formula (2'):

(2')

wherein
 $R^{3'}$ is a hydrogen atom;
 X' is a protected hydroxyl or amino group or a hydrocarbon group having 1 to 6 carbon atoms, which is substituted with a hydroxyl and/or amino group which may carry a protecting group which hydrocarbon group may further be substituted with a —COOH group;
 Y' is a hydrogen atom, a —COOH group or a hydrocarbon group having 1 to 6 carbon atoms, which hydrocarbon group may further be substituted with a —COOH group;
 for obtaining a water-soluble polymer comprising acidic groups; and optionally
b) a step of coupling a compound having a functional group reactive with an acidic group of repeating units derived from the first polymerizable monomer and/or a functional group reactive with hydroxyl group of repeating units derived from the second copolymerizable monomer to the water-soluble polymer comprising acidic groups obtained in step a), wherein the optionally protected acidic group or hydroxyl and/or amino group(s) is/are deprotected;
(C) a water-soluble, hydrolysis-stable monomer having a single polymerizable double bond and optionally a carboxylic acid group or hydroxyl group, which monomer is a (meth)acryl monomer represented by the general formula (3')

(3')

wherein
 $R^{5''}$ represents a hydrogen atom, a linear $C_{1-4}$ or branched or cyclic $C_{3-6}$ alkyl group which may be substituted with a cyclohexyl group or a phenyl group, or a $C_{3-6}$ cycloalkyl group which may be substituted with a $C_{1-4}$ alkyl group, most preferably, $R_{10}$ represents a hydrogen atom or a linear $C_{1-4}$ or branched or cyclic $C_{3-6}$ alkyl group;

G$^{\#"}$ is —OH or —NR$_6"$R*$_6"$ wherein R$_6"$ and R*$_6"$ independently represent a hydrogen atom, a linear C$_{1-10}$ or branched C$_{3-10}$ alkyl which may be substituted with a C$_{6-10}$ aryl group or —OH, a cyclic C$_{3-6}$ alkyl group which may be substituted by —OH, or R$_6"$ and R*$_6"$ independently represent a linear C$_{1-10}$ or branched C$_{3-10}$ alkyl group which cooperatively form a ring in which R$_6"$ and R*$_6"$ are linked by a C—C bond or an ether group; preferably a linear C$_{1-6}$ or branched C$_{3-6}$ alkyl group which may be substituted with a C$_{6-10}$ aryl group or —OH, a cyclic C$_{3-6}$ alkyl group, or R$_6"$ and R*$_6"$ independently represent a linear C$_{1-6}$ or branched C$_{3-6}$ alkyl group which cooperatively form a ring in which R$_6"$ and R*$_6"$ are linked by a C—C bond or an ether group; more preferably a methyl group, an ethyl group, a 2-hydroxyethyl group, a n-propyl group, a benzyl group, an α-methylbenzyl group, a cyclohexyl group, an adamantyl group, or R$_6"$ and R*$_6"$ cooperatively form a N-piperidinyl or N-morpholinyl ring; most preferably R$_6"$ and R*$_6"$ independently represent a methyl or ethyl group;

preferably compound of formula (3') is a (meth)acrylamide compound selected from the group consisting of 2-hydroxyethyl acrylamide (HEAA), N,N-dimethyl(meth)acrylamide, N,N-di-n-propyl(meth)acrylamide, and N-ethyl-N-methyl(meth)acrylamide; most preferably compound of formula (6") is selected from the group consisting of 2-hydroxyethyl acrylamide (HEAA), N,N-dimethyl(meth)acrylamide, N,N-diethyl(meth)acrylamide, N,N-di-n-propyl(meth)acrylamide, and N-ethyl-N-methyl(meth)acrylamide (D) a water-soluble, hydrolysis-stable polymerizable crosslinker having at least two polymerizable carbon-carbon double bonds, which crosslinker is represented by the general formula (4):

$$A"\text{-L(B)}_{n'} \qquad (4)$$

wherein
A" is a group of the following formula (5)

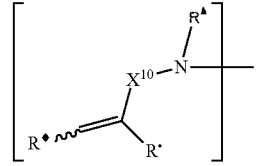

(5)

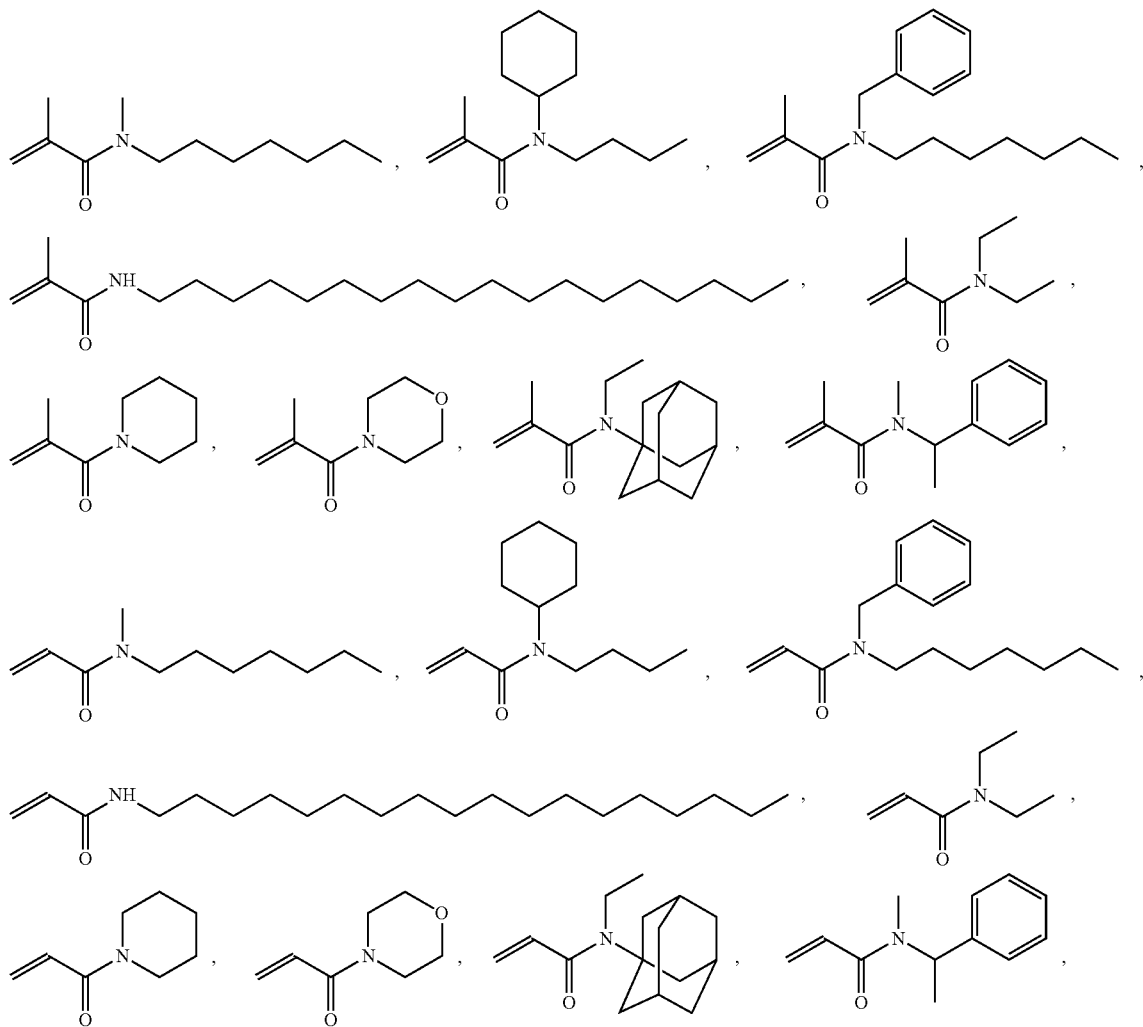

$X^{10}$ is CO, CS, $CH_2$, or a group $[X^{100}Z^{10}]_k$, wherein $X^{100}$ is an oxygen atom, a sulfur atom or NH, $Z^{10}$ is a linear $C_{1-4}$ or branched $C_{3-6}$ alkylene group, and k is an integer of from 1 to 10;

$R^\blacklozenge$ is a hydrogen atom, $-COOM^{10}$, a linear $C_{1-4}$ or branched $C_{3-6}$ alkyl group,
a $C_{3-6}$ cycloalkyl group, or
a $C_{6-14}$ aryl or $C_{3-14}$ heteroaryl group, $R^\bullet$ is a hydrogen atom,
$-COOM^{10}$
a linear $C_{1-4}$ or branched $C_{3-6}$ alkyl group,
a $C_{3-6}$ cycloalkyl group, or
a $C_{6-14}$ aryl or $C_{3-14}$ heteroaryl group, $R^\blacktriangle$ is a hydrogen atom,
a linear $C_{1-6}$ or branched $C_{3-6}$ alkyl or linear $C_{2-6}$ or branched $C_{3-6}$ alkenyl group which may be substituted with a $C_{6-10}$ aryl, preferably $R^\blacktriangle$ is a methyl group, an ethyl group, an allyl group or a benzyl group, most preferably an ethyl group or an allyl group;

L is a single bond or a linker group represented by a straight chain, branched and/or cyclic, saturated or unsaturated aliphatic, divalent $C_{2-12}$ hydrocarbon group which may contain 1 to 3 heteroatoms selected from oxygen, nitrogen and sulphur;

B is selected from:
(i) a group according to the definition of A",
(ii) a group of the following formula (6)

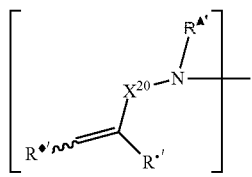

(6)

wherein
$X^{20}$ independently has the same meaning as defined for $X^1$ in formula (5),
$R^{\blacklozenge\prime}$ and $R^{\bullet\prime}$ are independent from each other and independently have the same meaning as defined for $R^\blacklozenge$ and $R^\bullet$ of formula (5),
$R^{\blacktriangle\prime}$ is a hydrogen atom,
a linear $C_{1-4}$ or branched $C_{3-6}$ alkyl group,
a $C_{3-6}$ cycloalkyl group,
a $C_{6-14}$ aryl group,
(iii) a group of the following formula (IV)

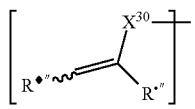

(7)

wherein
$X^{30}$ is CO, $-CH_2CO-$, CS, or $-CH_2CS-$,
$R^{\blacklozenge\prime\prime}$ and $R^{\bullet\prime\prime}$ which are independent from each other and independently have the same meaning as $R^\blacklozenge$ and $R^\bullet$ defined for formula (5), or
(iv) a group $[X^{40}Z^{200}]_p E$,
wherein
$Z^{200}$ is a linear $C_{1-4}$ or branched $C_{3-6}$ alkylene group,
$X^{40}$ is an oxygen atom, a sulfur atom or NH, E is a hydrogen atom,
$PO_3M_2$,
a linear $C_{1-4}$ or branched $C_{3-6}$ alkyl group,
a $C_{3-6}$ cycloalkyl group,
a $C_{6-14}$ aryl or $C_{3-14}$ heteroaryl group, and
p is an integer of from 1 to 10;
and
n' is an integer of from 1 to 4;
wherein $M^{10}$ which are independent from each other each represent hydrogen atom or a metal atom;
preferably the crosslinker represented by the general formula (4) is selected from the group consisting of 1,3-bisacrylamido-propan (BAP), 1,3-bisacrylamido-2-ethyl-propan (BAPEN), N,N-di(allyl acrylamido) propane and compounds having the following structural formulae:

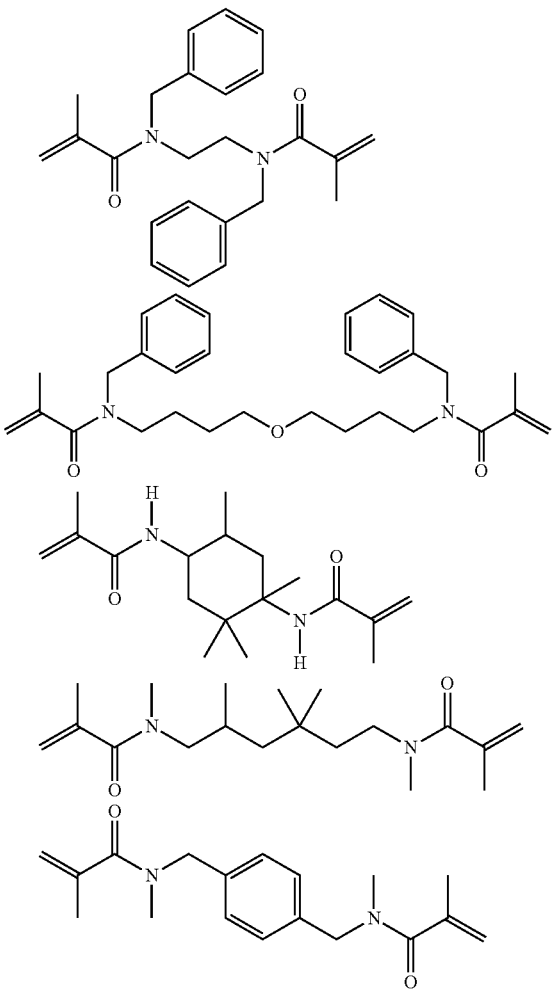

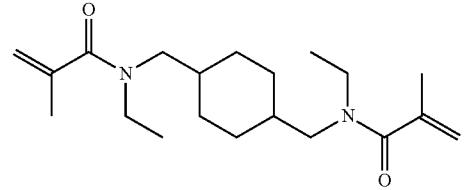

45
-continued
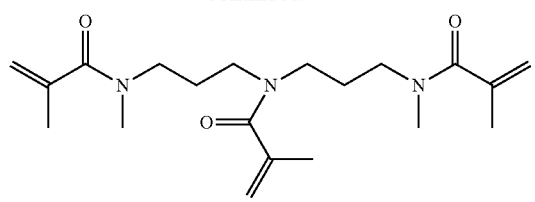
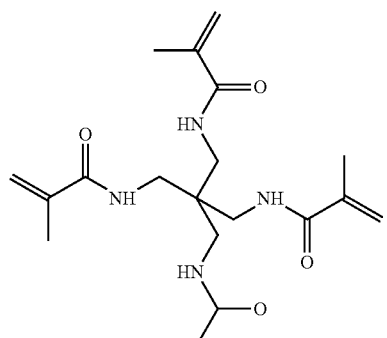
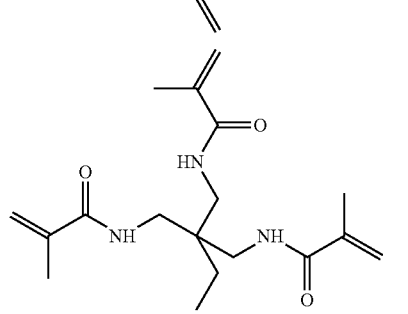
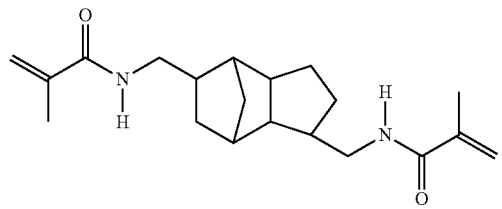
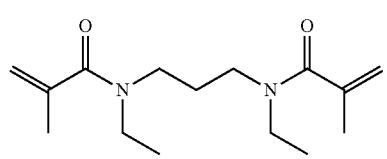
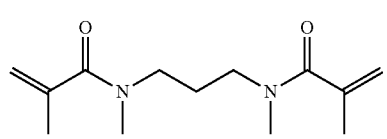
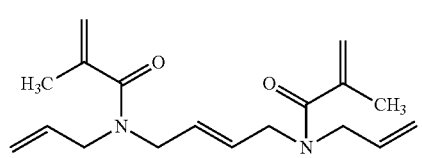
46
-continued
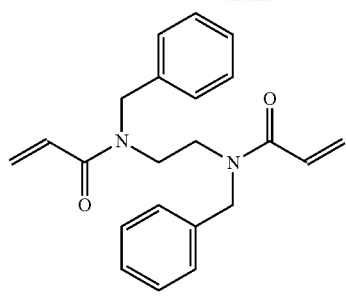
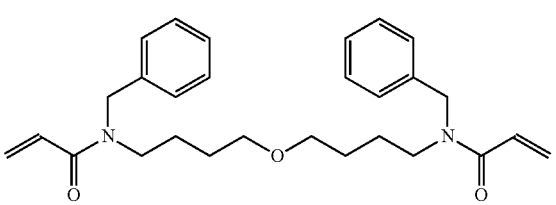
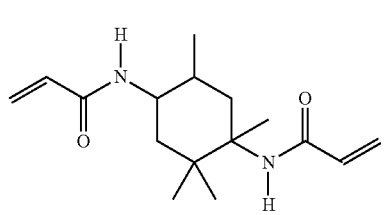
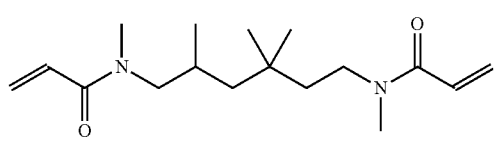
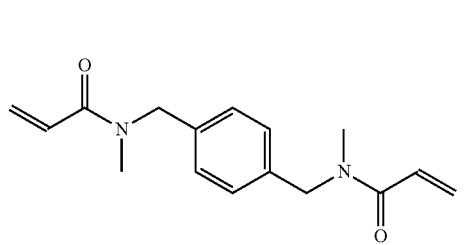
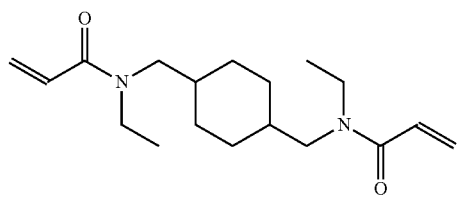
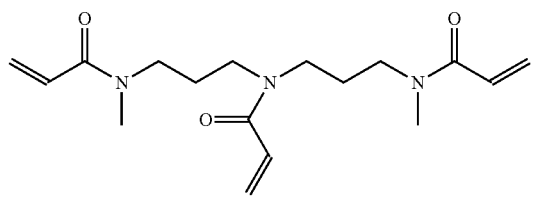

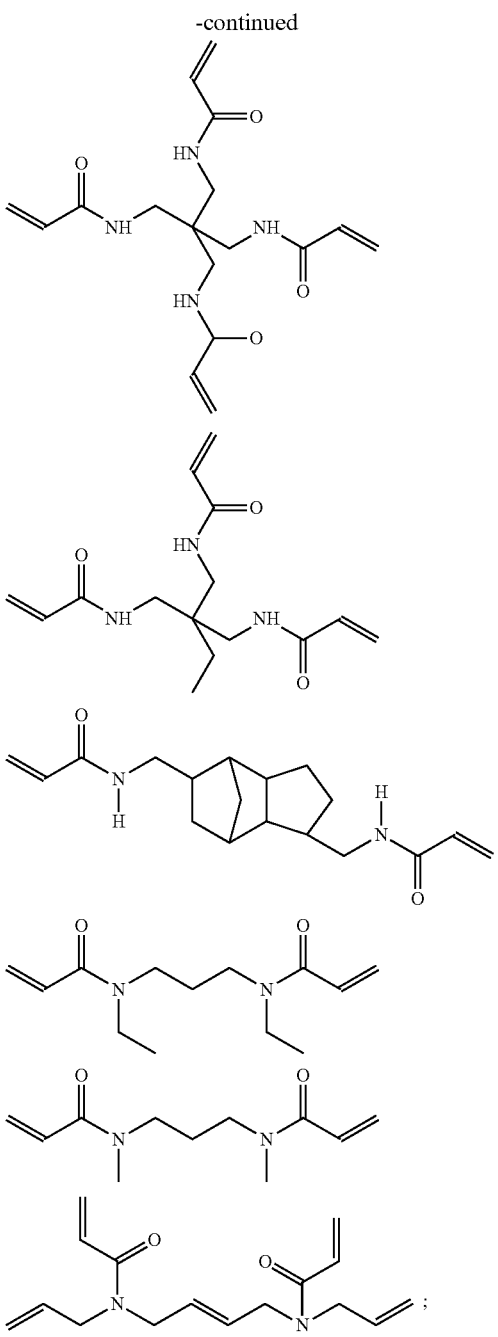

most preferably, the crosslinker of formula (4) is selected from the group consisting of N,N'-(2E)-but-2-en-1,4-diallylbis-[(N-prop-2-en-1) amide (BAABE), N,N'-diethyl-1,3-bisacrylamido-propan (BADEP), 1,3-bisacrylamido-propan (BAP), 1,3-bisacrylamido-2-ethyl-propan (BAPEN) and N,N-di(allyl acrylamido) propane, more preferably, the crosslinker of formula (4) is N,N'-(2E)-but-2-en-1,4-diallylbis-[(N-prop-2-en-1) amide (BAABE) or N,N'-diethyl-1,3-bisacrylamido-propan (BADEP);

or the water-soluble, hydrolysis-stable polymerizable crosslinker according to (D) is represented by a macromonomer of the following formula (8):

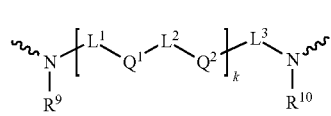

wherein

A is a linker group represented by the following formula (10), wherein the nitrogen atom of at least two of the termini forms an amide bond with a substitutent X:

$$\text{(10)}$$

wherein $R^9$ and $R^{10}$ independently represent a hydrogen atom or a substituted or unsubstituted aliphatic or cycloaliphatic hydrocarbon group, preferably $R^9$ and $R^{10}$ independently represent a hydrogen atom or a linear $C_{1-6}$ or branched or cyclic $C_{3-8}$ alkyl group, more preferably a linear $C_{1-3}$ or a branched $C_{3-5}$ alkyl group;

$L^1$, $L^2$, and $L^3$ independently represent a single bond, or a linear $C_{2-10}$ or branched or cyclic $C_{3-10}$ hydrocarbon group containing from 1 to 3 heteroatoms selected from nitrogen and oxygen in the backbone of the hydrocarbon group, and optionally from 1 to 3 functional groups selected from carboxylic acid groups or a salt thereof, hydroxyl groups, thiol groups and amino groups;

$Q_1$ and $Q_2$, may be the same or different and represent a single bond or a linkage selected from an amide, a urethane, a urea and a thiourea linkage, preferably a single bond or an amide linkage, k is an integer of at least 0;

X are moieties containing a polymerizable double bond and forming an amide bond with a nitrogen atom of A, which X may be the same or different and are represented by the following formula (9):

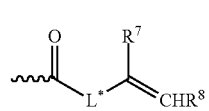

wherein $R^7$ and $R^8$ are independent from each other and represent a hydrogen atom, a linear $C_{1-6}$ or branched or cyclic $C_{3-8}$ alkyl group or a group —$(CH_2)_m$—COOM, wherein M is a hydrogen atom or a metal atom and m is an integer of from 0 to 6, L* is a bond or a linear $C_{1-6}$ or branched or cyclic $C_{3-8}$ alkylene group, preferably a single bond or a methylene or ethylene group, and n is an integer of at least one, preferably 2 to 4, most preferably 2; preferably the crosslinker in the form of the macromonomer of formula (8) is a (meth)acrylamide compound having the following structural formula:

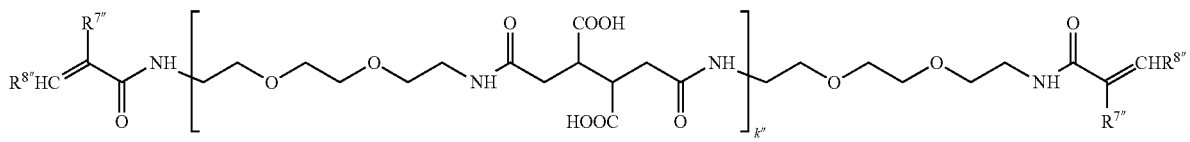

wherein

R$^{7''}$ is a hydrogen atom or a methyl group and
R$^{8''}$ is a hydrogen atom or a group —(CH$_2$)$_m$—COOH, wherein m is 0, 1 or 2, most preferably R$^{7''}$ and R$^{8''}$ are a hydrogen atom, and
k'' is an integer from 3 to 20, most preferably from 5 to 10; and (E) a polymerization initiator system based on a radical initiator in the form of a photoinitiator or a redox initiator or a mixture thereof.

The disclosure will now be further illustrated by the following Examples.

EXAMPLES

Preparation of (B) a Water-Soluble Polymer Comprising Acidic Groups

By way of example for component (B) of the present aqueous dental glass ionomer composition, poly(acrylic acid-co-itaconic anhydride) (PAA-IAA) having the following structural formula:

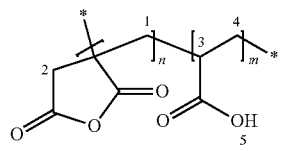

was prepared as follows:

In a 100 mL two-neck bottle, equipped with a septum and reflux condenser, 9.5 mL (139 mmol) acrylic acid (AA) are placed and 22.4 mL (33 wt.-%) distilled ethyl acetate or alternatively 22.4 mL 1,4-dioxane are added. 0.3-15.6 g (2.8-139 mmol) itaconic acid anhydride (IAA) solved in 0.7-36.4 distilled ethyl acetate (or dioxane) as well as 230-456 mg (1 mol-%) azoisobutyronitrile (AIBN) are added and the clear solution is gently purged with nitrogen for 30 minutes. The polymerization is initiated by heating the mixture up to 70° C. (oil bath) for 4 h. During the whole reaction a nitrogen blanket is kept over the liquid. The precipitate from the polymerization in ethyl acetate is collected via filtration and reprecipitated from 20 mL 1,4 dioxane in 200 mL acetonitrile.

The polymer from the solution-polymerization in dioxane is collected via precipitation in a 10-fold excess of acetonitrile.

In both cases, the obtained, colorless solid is dried under reduced pressure at 50° C.

$^1$H-NMR (300 MHz, DMSO-d$_6$): δ [ppm]=12.3 (br, 5), 3.4 (br, 2), 2.2 (br, 3), 1.7 (br, 1 and 4).

GPC (water): averaged M$_n$=2.900-3.600 g/mol, averaged M$_w$=15.000-47.400 g/mol, D=5.1-14.6

DSC: T$_g$=64° C. (AA:IAA=1:1)-96° C. (AA:IAA=50:1)

Preparation of Aqueous Dental Glass Ionomer Compositions and Testing of Cured Compositions Aqueous dental glass ionomer compositions of Example 1 according to the disclosure and of the Comparative Examples 1 and 2 have been prepared by forming a liquid composition of the ingredients listed in Table 1 below, which add up to 100 wt %, and admixing the liquid composition with a reactive particulate glass powder in a powder/liquid ratio of 2.8/1. In Comparative Example 3, the commercial glass ionomer restorative Chemfil Rock® already contains glass powder, and thus, no glass powder was admixed thereto.

The dental glass ionomer compositions of Example 1 and Comparative Examples 1 to 3 were cured by a dental curing light. For the resulting cured dental glass ionomer composition, the flexural strength has been determined according to ISO 4049.

TABLE 1

Compositions of Example 1 and Comparative Examples 1 and 2, and flexural strength determined for the cured dental glass ionomer compositions of Example 1 and Comparative Examples 1 to 3

| Composition of: | PAA-IAA [wt %] | AA [wt %] | HEAA [wt %] | BADEP [wt %] | water [wt %] | initiator/ inhibitor [wt %] | flexural strength [MPa] |
|---|---|---|---|---|---|---|---|
| Example 1 | 25.000 | 15.000 | 10.000 | 15.000 | 33.855 | 1.145 | 88 |
| Comparative Example 1 | 25.000 | 0.000 | 0.000 | 35.000 | 38.855 | 1.145 | 70 |
| Comparative Example 2 | 25.000 | 25.000 | 10.000 | 0.000 | 38.855 | 1.145 | 64 |
| Comparative Example 3 | Chemfil Rock® | | | | | | 35 |

Legend of abbreviations:
PAA-IAA poly(acrylic acid-co-itaconic anhydride)
AA acrylic acid
HEAA 2-hydroxyethylacryl amide
BADEP 1,3-bis(acrylamido)-N,N'-diethylpropane
initiator camphor quinone, dimethylamino benzontitrile
inhibitor tert.-butylhydroquinone
Chemfil Rock ® commercial glass ionomer restorative from Dentsply DeTrey GmbH

The invention claimed is:

1. An aqueous dental glass ionomer composition comprising
   (A) a reactive particulate glass,
   (B) a water-soluble polymer comprising acidic groups, which is reactive with the particulate glass in a cement reaction,
   (C) a water-soluble, hydrolysis-stable monomer having a single polymerizable double bond and optionally a carboxylic acid group or hydroxyl group;
   (D) a water-soluble, hydrolysis-stable polymerizable crosslinker having at least two polymerizable carbon-carbon double bonds; and
   (E) a polymerization initiator system;
   wherein the water-soluble polymer comprising acidic groups according to (B) does not contain polymerizable double bonds; whereby the water-soluble polymer comprising acidic groups does not react with the water-soluble monomer according to (C) or the water-soluble, hydrolysis-stable polymerizable crosslinker according to (D), and wherein the water-soluble polymer comprising acidic groups has a molecular weight $M_w$ of from $10^3$ to $10^6$ Da.

2. The aqueous dental glass ionomer composition according to claim 1, further comprising by at least one of the following features:
   the aqueous dental glass ionomer composition does not comprise a polymerizable polymer having polymerizable double bond(s);
   the water-soluble polymer comprising acidic groups according to (A) (B) does not comprise pendant β-dicarbonyl group(s);
   the aqueous dental glass ionomer composition does not comprise at least one of the following components: unmodified polyacrylic acid as water-soluble polymer according to (B), acrylic acid as water-soluble monomer according to (C) and/or N,N'-diethyl-1,3-bisacrylamido-propan (BADEP) as crosslinker according to (D).

3. The aqueous dental glass ionomer composition according to claim 1, wherein the water-soluble, hydrolysis-stable monomer according to (C) has a molecular weight of at most 600 Da, and/or wherein the water-soluble, hydrolysis-stable polymerizable crosslinker according to (D) is a bis(meth)acryl amide.

4. The aqueous dental glass ionomer composition according to claim 1, further comprising at least one of the following features:
   the water-soluble, hydrolysis-stable monomer according to (C) is contained in an amount of from 1 to 10 percent by weight based on the total weight of the aqueous dental glass ionomer composition;
   water-soluble, hydrolysis-stable polymerizable crosslinker having at least two polymerizable carbon-carbon double bonds according to (D) is contained in an amount of from 1 to 10 percent by weight based on the total weight of the aqueous dental glass ionomer composition;
   the aqueous dental glass ionomer composition according to any one of the preceding claims, which further comprises (E) a non-reactive filler.

5. The aqueous dental glass ionomer composition according to claim 1, wherein the water-soluble polymer comprising acidic groups is obtainable by polymerizing a mixture containing one or more polymerizable monomers represented by the general formula (1a):

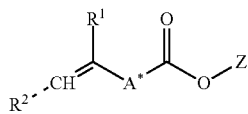

(1a)

wherein
$R^1$ is a hydrogen atom, a —COOZ group, a linear $C_{1-6}$ or branched or cyclic $C_{3-8}$ alkyl group which may be substituted with a COOZ group, or a $C_{6-10}$ aryl group which may be substituted with a —COOZ group;
$R^2$ is a hydrogen atom, a —COOZ group, or a linear $C_1$-6 or branched or cyclic $C_{3-8}$ alkyl group which may be substituted with a —COOZ group;
A* is a single bond, or a linear $C_{1-6}$ or branched or cyclic $C_{3-8}$ alkylene group, wherein if the carbon number of the alkylene group is two or more, then the alkylene group may contain 1 to 3 heteroatoms, wherein each heteroatom is located in between two carbon atoms of the alkylene carbon chain, which heteroatoms are selected from an oxygen atom, nitrogen atom, and sulfur atom, and/or which alkylene group may contain, if its carbon number is two or more, in between two carbon atoms of the alkylene carbon chain 1 to 3 groups selected from an amide bond or a urethane bond;
Z which may be the same or different, independently represents a hydrogen atom, a metal ion, a protecting group for a carboxylic acid group, or the Z forms with a further —COOZ group present in the molecule an intramolecular anhydride group.

6. The aqueous dental glass ionomer composition according to claim 5, wherein the mixture further comprises a copolymerizable monomer represented by the general formula (2):

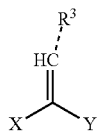

(2)

wherein
$R^3$ is a hydrogen atom or a linear $C_{1-6}$ or branched or cyclic $C_{3-8}$ alkyl group which may be substituted with a —COOZ' group;
X is a protected hydroxyl or amino group, or a hydrocarbon group having 1 to 20 carbon atoms, which is substituted by a hydroxyl and/or amino group which may carry a protecting group, wherein the hydrocarbon group may contain 1 to 6 heteroatoms, which heteroatoms are selected from an oxygen atom, nitrogen atom, and sulfur atom, and/or which hydrocarbon group may contain a group selected from an amide bond or a urethane bond and which hydrocarbon group may further be substituted by up to 6 groups selected from —COOZ', amino groups and thiol groups;
Y is a hydrogen atom, a —COOZ' group, or a hydrocarbon group having 1 to 20 carbon atoms, wherein the hydrocarbon group may contain 1 to 6 heteroatoms, which heteroatoms are selected from an oxygen atom, nitrogen atom, and sulfur atom, and/or which hydrocarbon group may contain a group selected from an amide bond or a urethane bond and which hydrocarbon group may further be substituted by up to 6 groups selected from —COOZ', amino groups, hydroxyl groups and thiol groups;

Z' which may be the same or different, independently represents a hydrogen atom, a metal ion, a protecting group for a carboxylic acid group, or the Z' forms with a further —COOZ' group present in the molecule an intramolecular anhydride group.

7. The aqueous dental glass ionomer composition according to claim 1, wherein the water-soluble, hydrolysis-stable monomer according to (C) is a compound represented by the general formula (3):

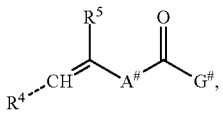

(3)

wherein
$A^\#$ is a single bond or a linear $C_{1-15}$ or branched or cyclic $C_{3-15}$ alkylene group, wherein if the carbon number of the alkylene group is two or more, then the alkylene group may contain 1 to 3 heteroatoms, wherein each heteroatom is located in between two carbon atoms of the alkylene carbon chain, which heteroatoms are selected from an oxygen atom, nitrogen atom, and sulfur atom, and/or which alkylene group may contain, if its carbon number is two or more, in between two carbon atoms of the alkylene carbon chain 1 to 3 groups selected from an amide bond or a urethane bond; preferably, $A^\#$ is a single bond or a linear $C_{1-6}$ or branched or cyclic $C_{3-5}$ alkylene group;
$R^4$ is a hydrogen atom, a —COOZ$^\#$ group, or a linear $C_{1-6}$ or branched or cyclic $C_{3-8}$ alkyl group which may be substituted with a —COOZ$^\#$ group;
$R^5$ represents a hydrogen atom, —COOM, a linear $C_1$ to $C_{18}$ or branched $C_3$ to $C_{18}$ alkyl group which may be substituted with a CM cycloalkyl group, a $C_{8-14}$ aryl or $C_{3-14}$ heteroaryl group, —OM*, —COOM, —PO$_3$M, —O—PO$_3$M$_2$ or —SO$_3$M, a $C_3$ to $C_{18}$ cycloalkyl group which may be substituted with a $C_{1-16}$ alkyl group, a $C_{8-14}$ aryl or $C_{3-14}$ heteroaryl group, —OM*, —COOM, —PO$_3$M, —O—PO$_3$M$_2$ or —SO$_3$M, or a $C_5$ to $C_{18}$ aryl or $C_3$ to $C_{18}$ heteroaryl group which may be substituted with —OM*, —COOM, —PO$_3$M, —O—PO$_3$M$_2$ or —SO$_3$M,
$G^\#$ is —OH or —NR$_6$R*$_6$ wherein R$_6$ and R*$_6$ independently represent a hydrogen atom, a linear $C_1$ to $C_{18}$ or branched $C_3$ to $C_{18}$ alkyl group which may be substituted with a $C_{3-6}$ cycloalkyl group, a $C_{6-14}$ aryl or $C_{3-14}$ heteroaryl group, —OM*, —COOM, —PO$_3$M, —O—PO$_3$M$_2$ or —SO$_3$M, a $C_3$ to $C_{18}$ cycloalkyl group which may be substituted with a $C_{1-16}$ alkyl group, a $C_{8-14}$ aryl or $C_{3-14}$ heteroaryl group, —OM*, —COOM, —PO$_3$M, —O—PO$_3$M$_2$ or —SO$_3$M, or a $C_5$ to $C_{18}$ aryl or $C_3$ to $C_{18}$ heteroaryl group which may be substituted with —OM*, —COOM, —PO$_3$M, —O—PO$_3$M$_2$ or —SO$_3$M,
wherein R$_6$ and R*$_6$ may cooperatively form a ring in which R$_8$ and R*$_6$ are linked by a C—C bond or a functional group selected from the group consisting of an ether group, a thioether group, an amine group and an amide group,
Z$^\#$ which may be the same or different, independently represents a hydrogen atom, a metal ion, a protecting group for a carboxylic acid group, or the Z$^\#$ forms with a further —COOZ$^\#$ group present in the molecule an intramolecular anhydride group,
wherein M* of any one R$_{10}$, R$_{11}$ and R*$_{11}$, which M* are independent from each other, each represent a hydrogen atom or a hydroxyl-protecting group, and M of any one R$^5$, R$_6$ and R*$_6$, which M are independent from each other, each represent a hydrogen atom, a carboxyl-protecting group or a metal atom.

8. The aqueous dental glass ionomer composition according to claim 7, wherein the water-soluble, hydrolysis-stable monomer is a (meth)acryl monomer represented by the general formula (3')

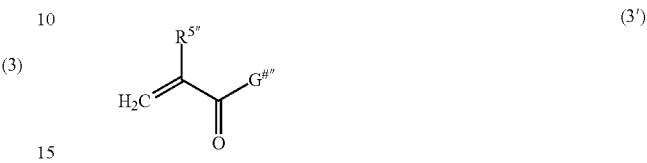

wherein
$R^{5''}$ represents a hydrogen atom, a linear $C_{1-4}$ or branched or cyclic $C_{3-5}$ alkyl group which may be substituted with a cyclohexyl group or a phenyl group, or a $C_{3-6}$ cycloalkyl group which may be substituted with a $C_{1-4}$ alkyl group, most preferably, $R_{10}$ represents a hydrogen atom or a linear $C_{1-4}$ or branched or cyclic $C_{3-6}$ alkyl group;
$G^{\#''}$ is —OH or —NR$_6$''R*$_6$'' wherein R$_6$'' and R*$_6$'' independently represent a hydrogen atom, a linear $C_{1-10}$ or branched $C_{3-10}$ alkyl which may be substituted with a $C_{6-10}$ aryl group or —OH, a cyclic $C_{3-10}$ alkyl group which may be substituted with —OH, or R$_6$'' and R*$_6$'' independently represent a linear $C_{1-10}$ or branched $C_{3-10}$ alkyl group which cooperatively form a ring in which R$_6$'' and R*$_6$'' are linked by a C—C bond or an ether group; preferably a linear $C_{1-6}$ or branched $C_{3-6}$ alkyl group which may be substituted with a $C_{6-10}$ aryl group or —OH, a cyclic $C_{3-6}$ alkyl group, or R$_6$'' and R*$_6$'' independently represent a linear $C_{1-6}$ or branched $C_{3-6}$ alkyl group which cooperatively form a ring in which R$_6$'' and R*$_6$'' are linked by a C—C bond or an ether group; more preferably a methyl group, an ethyl group, a 2-hydroxyethyl group, a n-propyl group, a benzyl group, an α-methylbenzyl group, a cyclohexyl group, an adamantyl group, or R$_6$'' and R*$_6$'' cooperatively form a N-piperidinyl or N-morpholinyl ring; most preferably R$_6$'' and R*$_6$'' independently represent a methyl or ethyl group.

9. The aqueous dental glass ionomer composition according to any one of the preceding claims, further comprising at least one of the following features:
the particulate glass comprises
1) 20 to 45% by weight of silica,
2) 20 to 40% by weight of alumina,
3) 20 to 40% by weight of strontium oxide,
4) 1 to 10% by weight of $P_2O_5$, and
5) 3 to 25% by weight of fluoride;
aqueous dental glass ionomer composition comprises 20 to 80 percent by weight of the reactive particulate glass, based on the total weight of the composition and/or comprises 10 to 80 percent by weight of the polymer comprising acidic groups, based on the total weight of the composition, and/or comprises up to 75 percent by weight of dispersed nanoparticles based on the total weight of the composition.

10. The aqueous dental glass ionomer composition according to claim 1, wherein the water-soluble, hydrolysis-stable polymerizable crosslinker according to (D) is represented by the general formula (4):

(4)

wherein

A" is a group of the following formula (5)

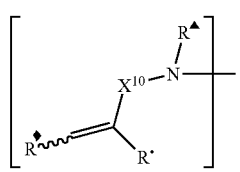
(5)

$X^{10}$ is CO, CS, $CH_2$, or a group $[X^{100}Z^{10}]_k$, wherein $X^{100}$ is an oxygen atom, a sulfur atom or NH, $Z^{10}$ is a linear $C_{1-4}$ or branched or cyclic $C_{3-6}$ alkylene group, and k is an integer of from 1 to 10;

$R^♦$ is a hydrogen atom, —$COOM^{10}$, a linear $C_{1-16}$ or branched $C_{3-16}$ alkyl group which may be substituted with a $C_{3-6}$ cycloalkyl group, a $C_{6-14}$ aryl or $C_{3-14}$ heteroaryl group, —$COOM^{10}$, —$PO_3M^{10}$, —O—$PO_3M^{10}_2$ or —$SO_3M^{10}$, a $C_{3-6}$ cycloalkyl group which may be substituted with a linear $C_{1-16}$ or branched $C_{3-16}$ alkyl group, a $C_{6-14}$ aryl or $C_{3-14}$ heteroaryl group, —$COOM^{10}$, —$PO_3M^{10}$, —O—$PO_3M^{10}_2$ or —$SO_3M^{10}$, a $C_{6-14}$ aryl or $C_{3-14}$ heteroaryl group which may be substituted with —$COOM^{10}$, —$PO_3M^{10}$, —O—$PO_3M^{10}_2$ or —$SO_3M^{10}$, $R^•$ is a hydrogen atom,

—$COOM^{10}$ a linear $C_{1-16}$ or branched $C_{3-16}$ alkyl group which may be substituted with a $C_{6-14}$ aryl or $C_{3-14}$ heteroaryl group, —$COOM^{10}$, —$PO_3M^{10}$, —O—$PO_3M^{10}_2$ and —$SO_3M^{10}$, a $C_{3-6}$ cycloalkyl group which may be substituted with a linear $C_{1-16}$ alkyl or branched $C_{3-16}$ group, a $C_{6-14}$ aryl or $C_{3-14}$ heteroaryl group, —$COOM^{10}$, —$PO_3M^{10}$, —O—$PO_3M^{10}_2$ or —$SO_3M^{10}$, or a $C_{6-14}$ aryl or $C_{3-14}$ heteroaryl group which may be substituted with —$COOM^{10}$, —$PO_3M^{10}$, —O—$PO_3M^{10}_2$ and —$SO_3M^{10}$, $R^▲$ is a hydrogen atom, a linear $C_{1-16}$ or branched $C_{3-16}$ alkyl or linear $C_{2-16}$ or branched $C_{3-16}$ alkenyl group which may be substituted with a $C_{3-6}$ cycloalkyl group, a $C_{6-14}$ aryl or $C_{3-14}$ heteroaryl group, —$COOM^{10}$, —$PO_3M^{10}$, —O—$PO_3M^{10}_2$ or —$SO_3M^{10}$, a $C_{3-6}$ cycloalkyl group which may be substituted with a linear $C_{1-16}$ or branched $C_{3-16}$ alkyl group, a $C_{6-14}$ aryl or $C_{3-14}$ heteroaryl group, —$COOM^{10}$, —$PO_3M^{10}$, —O—$PO_3M^{10}_2$ or —$SO_3M^{10}$, a $C_{6-14}$ aryl group which may be substituted with —$COOM^{10}$, —$PO_3M^{10}$, —O—$PO_3M^{10}_2$ or —$SO_3M^{10}$, preferably $R^▲$ is a linear $C_{1-10}$ or branched $C_{3-10}$ alkyl or linear $C_{2-10}$ or branched $C_{3-10}$ alkenyl group which may be substituted with a $C_{4-6}$ cycloalkyl group, a $C_{6-10}$ aryl or $C_{6-10}$ heteroaryl group, more preferably $R^▲$ is a linear $C_{1-6}$ or branched $C_{3-6}$ alkyl or alkenyl group which may be substituted with a $C_{6-10}$ aryl, even more preferably $R^▲$ is a methyl group, an ethyl group, an allyl group or a benzyl group, most preferably an ethyl group or an allyl group, L is a single bond or a linker group;

B is selected from:
(i) a group according to the definition of A",
(ii) a group of the following formula (6)

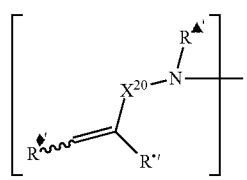
(6)

wherein $X^{20}$ independently has the same meaning as defined for $X'$ in formula (5), $R^{▲'}$ and $R^{•'}$ are independent from each other and independently have the same meaning as defined for $R^▲$ and $R^•$ of formula (5), $R^{▲'}$ is a hydrogen atom, a linear $C_{1-16}$ or branched $C_{3-16}$ alkyl group which may be substituted with a $C_{3-6}$ cycloalkyl group, a $C_{6-14}$ aryl or $C_{3-14}$ heteroaryl group, —$COOM^{10}$, —$PO_3M^{10}$, —O—$PO_3M^{10}_2$ or —$SO_3M^{10}$, a $C_{3-6}$ cycloalkyl group which may be substituted with a linear $C_{1-16}$ or branched $C_{3-16}$ alkyl group, a $C_{6-14}$ aryl or $C_{3-14}$ heteroaryl group, —$COOM^{10}$, —$PO_3M^{10}$, —O—$PO_3M^{10}_2$ or —$SO_3M^{10}$, a $C_{6-14}$ aryl group which may be substituted with —$COOM^{10}$, —$PO_3M^{10}$, —O—$PO_3M^{10}_2$ or —$SO_3M^{10}$, (iii) a group of the following formula (IV)

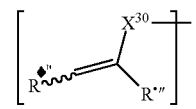
(7)

wherein $X^{30}$ is CO, —$CH_2CO$—, CS, or —$CH_2CS$—, $R^{▲"}$ and $R^{•"}$ which are independent from each other and independently have the same meaning as $R^▲$ and $R^•$ defined for formula (5), or (iv) a group $[X^{40}Z^{200}]_pE$, wherein $Z^{200}$ is a linear $C_{1-4}$ or branched or cyclic $C_{3-6}$ alkylene group, $X^{40}$ is an oxygen atom, a sulfur atom or NH, E is a hydrogen atom, $PO_3M_2$, a linear $C_{1-16}$ or branched $C_{3-16}$ alkyl group which may be substituted with a $C_{3-6}$ cycloalkyl group, a $C_{6-14}$ aryl or $C_{3-14}$ heteroaryl group, —$COOM^{10}$, —$PO_3M^{10}$, —O—$PO_3M^{10}_2$ or —$SO_3M^{10}$, a $C_{3-6}$ cycloalkyl group which may be substituted with a linear $C_{1-16}$ or branched $C_{3-16}$ alkyl group, a $C_{6-14}$ aryl or $C_{3-14}$ heteroaryl group, —$COOM^{10}$, —$PO_3M^{10}$, —O—$PO_3M^{10}_2$ or —$SO_3M_{10}$, a $C_{6-14}$ aryl or $C_{3-14}$ heteroaryl group which may be substituted with —$COOM^{10}$, —$PO_3M_{10}$, —O—$PO_3M_{10}^2$ or —$SO_3M^{10}$, and p is an integer of from 1 to 10;

and n' is an integer of from 1 to 4;

wherein $M^{10}$ which are independent from each other each represent a hydrogen atom or a metal atom.

11. The aqueous dental glass ionomer composition according to claim 10, wherein the water-soluble, hydrolysis-stable polymerizable crosslinker according to (D) is selected from the group consisting of 1,3-bisacrylamido-propan (BAP), 1,3-bisacrylamido-2-ethyl-propan (BAPEN), N,N-di(allyl acrylamido) propane and compounds having the following structural formulae:
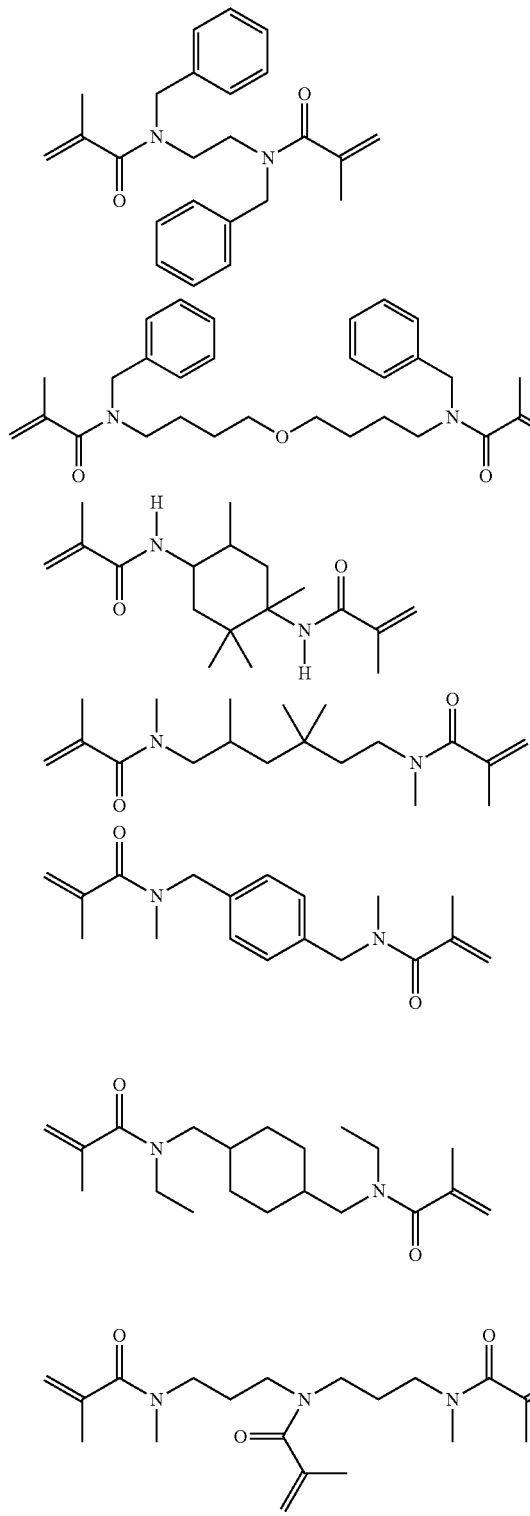
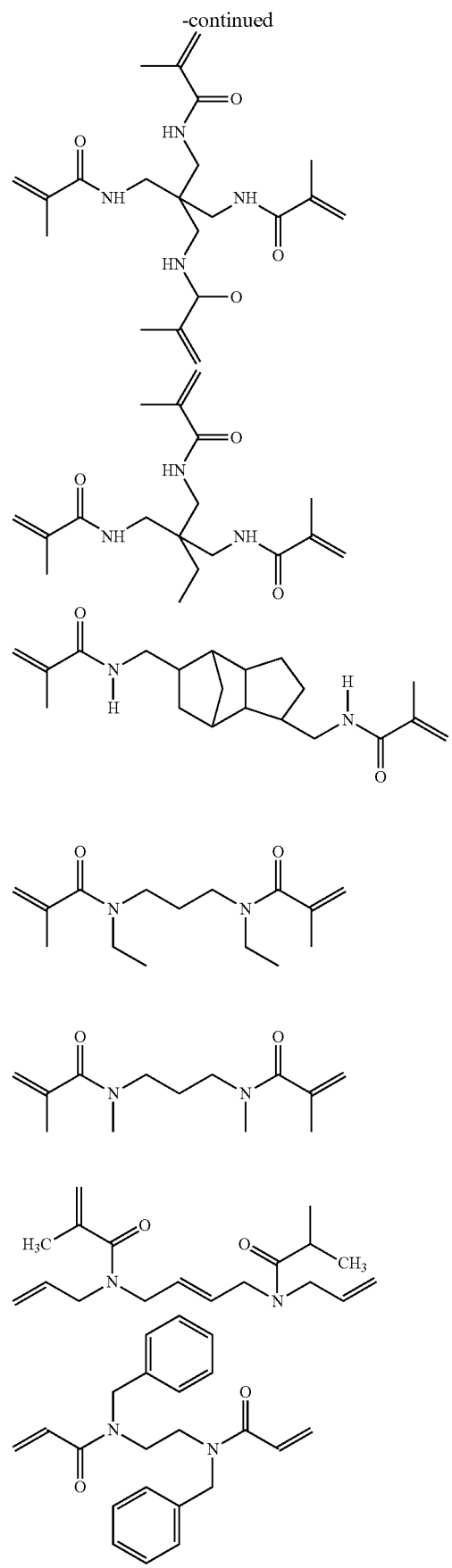

-continued

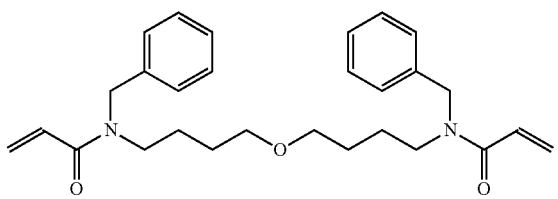
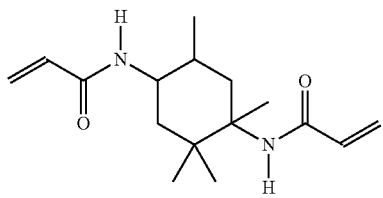
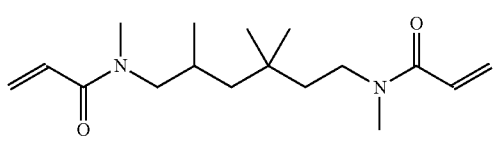
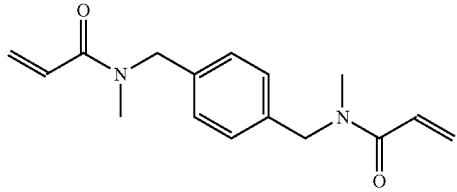
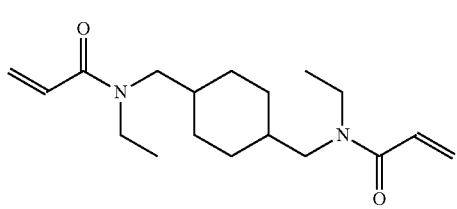
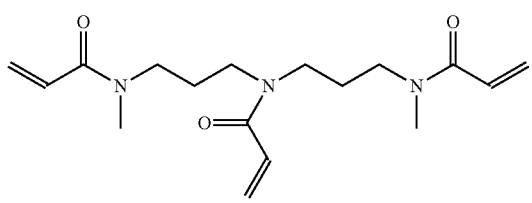
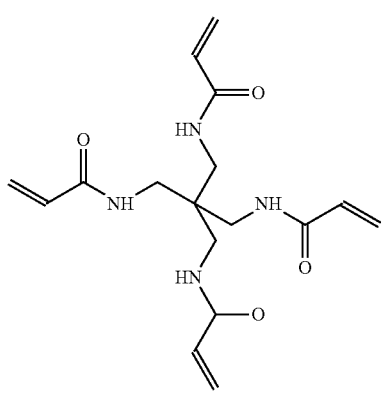

-continued

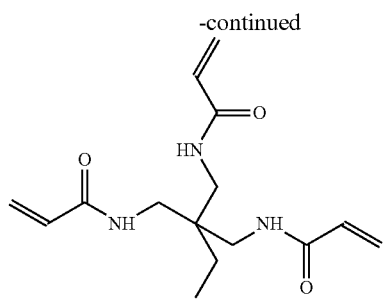
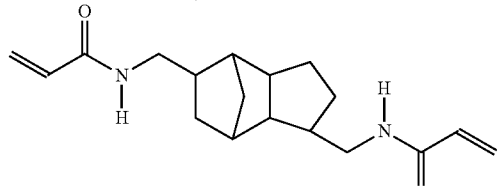
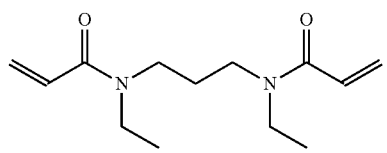
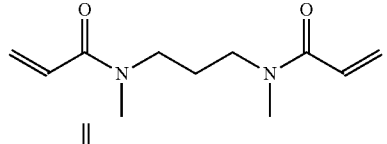
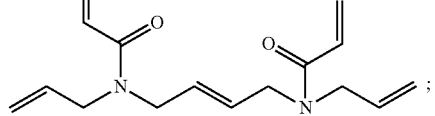

12. The aqueous dental glass ionomer composition according to claim 1, wherein the water-soluble, hydrolysis-stable polymerizable crosslinker according to (D) is represented by a macromonomer of the following formula (8):

$$AX_n \quad (8),$$

wherein

A is a linear or branched linker group containing at least n nitrogen atoms, whereby the linker group A has polyoxyalkylene and/or polyalkylene imine repeating units and optionally one or more acidic groups, and the linker group A has a valency of at least one which corresponds to the total number of substituents X, X are moieties containing a polymerizable double bond and forming an amide bond with a nitrogen atom of A, which X may be the same or different and are represented by the following formula (9)

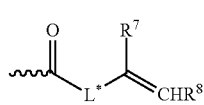

wherein $R^7$ and $R^8$ are independent from each other and represent a hydrogen atom, a linear $C_{1-6}$ or branched or cyclic $C_{3-6}$ alkyl group or a group —$(CH_2)_m$—COOM, wherein M is a hydrogen atom or a metal atom and m is an integer of from 0 to 6, the metal atom may be an alkali metal atom or an alkaline earth metal, wherein in case of an alkaline earth metal, the second charge on the metal atom is neutralized by either a further carboxylic acid anion or another anion, L* is a bond or a linear $C_{1-6}$ or branched or cyclic $C_{3-6}$ alkylene group, preferably a single bond or a methylene or ethylene group, and n is an integer of at least one.

13. The aqueous dental glass ionomer composition according to claim 12, wherein the water-soluble, hydrolysis-stable polymerizable crosslinker according to (D) is a compound having the following structural formula:

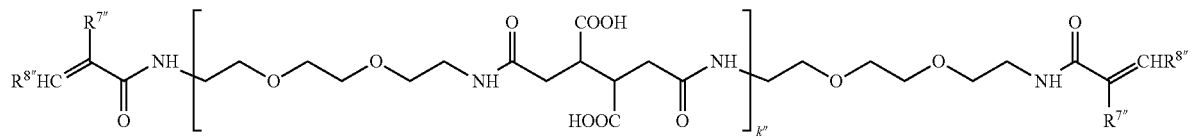

wherein
$R^{7''}$ is a hydrogen atom or a methyl group and
$R^{8''}$ is a hydrogen atom or a group —$(CH_2)_m$—COOH, wherein m is 0, 1 or 2, most preferably $R^{7'}$ and $R^{8'}$ are a hydrogen atom, and
k" is an integer from 3 to 20.

14. The aqueous dental glass ionomer composition according to claim 1, wherein upon curing, has at least one of the following mechanical characteristics:
an adhesive bond strength to dentin of at least 5 MPa as measured according to ISO 29022:2013; and/or
a flexural strength of at least 50 MPa as measured according to ISO 4049.

15. The aqueous dental glass ionomer composition according to claim 12, wherein A is a linker group represented by the following formula (10), wherein the nitrogen atom of at least two of the termini forms an amide bond with a substitutent X:

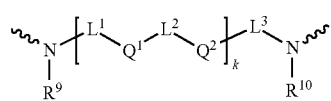

(10)

wherein $R^9$ and $R^{19}$ independently represent a hydrogen atom or a substituted or unsubstituted aliphatic or cycloaliphatic hydrocarbon group, preferably $R^9$ and $R^{19}$ independently represent a hydrogen atom or a linear $C_{1-6}$ or branched or cyclic $C_{3-6}$ alkyl group, more preferably a linear $C_{1-3}$ or branched $C_{3-5}$ alkyl group;

$L^1$, $L^2$, and $L^3$ independently represent a single bond, or a linear $C_{2-20}$ branched or cyclic $C_{3-20}$ hydrocarbon group containing from 1 to 6 heteroatoms selected from nitrogen and oxygen in the backbone of the hydrocarbon group, and optionally from 1 to 6 functional groups selected from carboxylic acid groups or a salt thereof, hydroxyl groups, thiol groups and amino groups;

$Q_1$ and $Q_2$, may be the same or different and represent a single bond or a linkage selected from an amide, a urethane, a urea and a thiourea linkage, k is an integer of at least 0.

16. The aqueous dental glass ionomer composition according to claim 8, wherein compound of formula (3') is a (meth)acrylamide compound selected from the group consisting of:

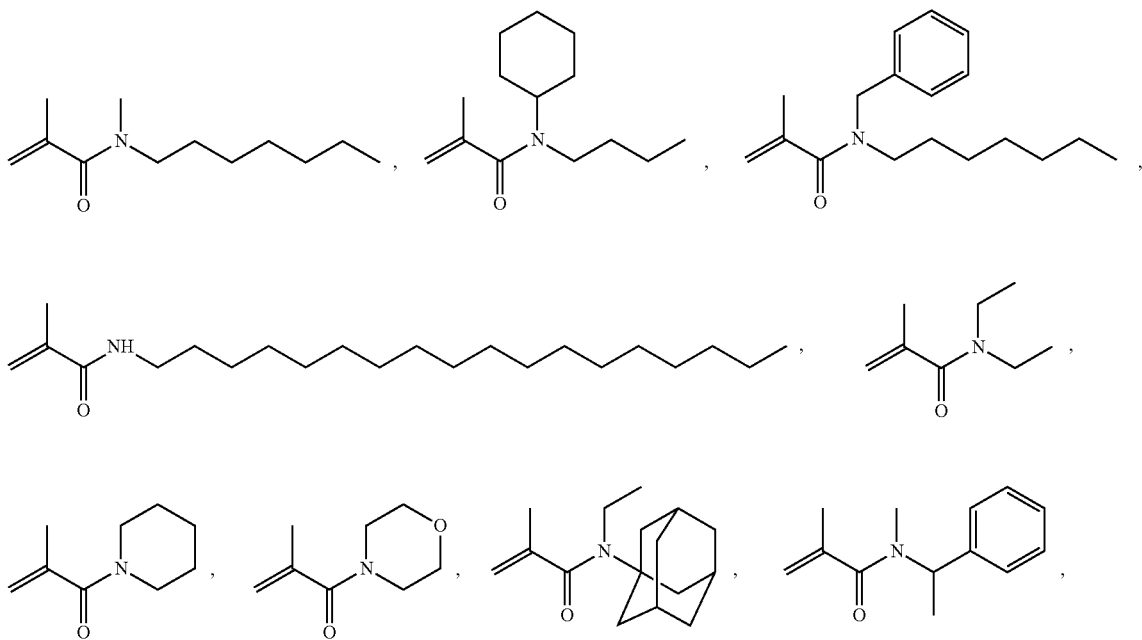

-continued

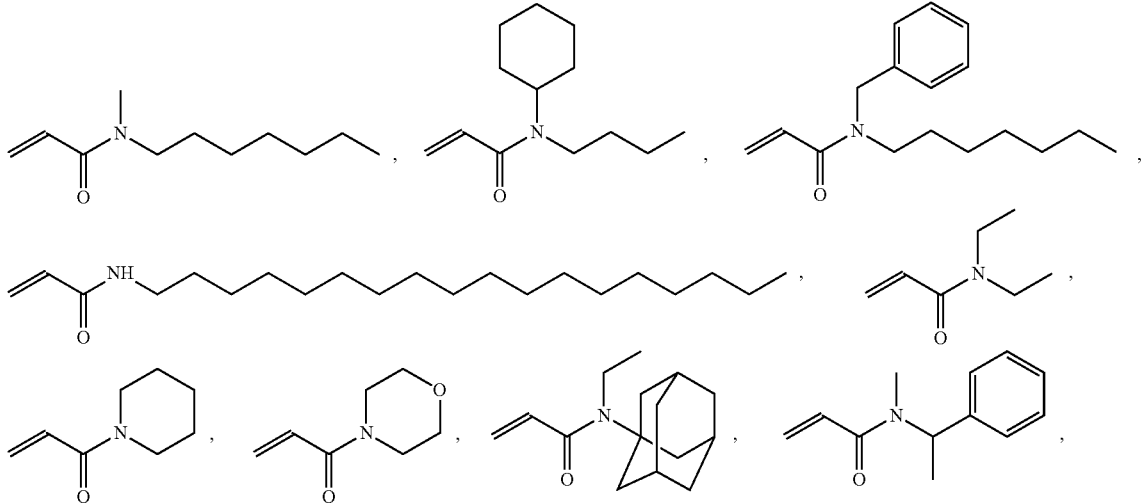

2-hydroxyethyl acrylamide (HEAA), N,N-dimethyl(meth)acrylamide, N,N-di-n-propyl(meth)acrylamide, and N-ethyl-N-methyl(meth)acrylamide.

17. The aqueous dental glass ionomer composition according to claim 10, wherein the crosslinker of formula (4) is selected from the group consisting of N,N'-(2E)-but-2-en-1,4-diallylbis-[(N-prop-2-en-1) amide (BAABE), N,N'-diethyl-1,3-bisacrylamido-propan (BADEP), 1,3-bisacrylamido-propan (BAP), 1,3-bisacrylamido-2-ethyl-propan (BAPEN) and N,N-di(allyl acrylamido) propane.

18. The aqueous dental glass ionomer composition according to claim 10, wherein the crosslinker of formula (4) is N,N'-(2E)-but-2-en-1,4-diallylbis-RN-prop-2-en-1) amide (BAABE) or N,N'-diethyl-1,3-bisacrylamido-propan (BADEP).

19. The aqueous dental glass ionomer composition according to claim 13, wherein k" is an integer from 5 to 10.

20. The aqueous dental glass ionomer composition according to claim 8, wherein the compound of formula (3') is selected from the group consisting of 2-hydroxyethyl acrylamide (HEAA), N,N-dimethyl(meth)acrylamide, N,N-diethyl(meth)acrylamide, N,N-di-n-propyl(meth)acrylamide, and N-ethyl-N-methyl(meth)acrylamide.

* * * * *